US010010882B2

(12) United States Patent
White et al.

(10) Patent No.: US 10,010,882 B2
(45) Date of Patent: Jul. 3, 2018

(54) MICROFLUIDIC DEVICES HAVING ISOLATION PENS AND METHODS OF TESTING BIOLOGICAL MICRO-OBJECTS WITH SAME

(71) Applicant: Berkeley Lights, Inc., Emeryville, CA (US)

(72) Inventors: Mark P. White, San Francisco, CA (US); Eric D. Hobbs, Livermore, CA (US); J. Tanner Nevill, El Cerrito, CA (US); Daniele Malleo, El Cerrito, CA (US); Steven W. Short, Pleasanton, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 467 days.

(21) Appl. No.: 14/520,568

(22) Filed: Oct. 22, 2014

(65) Prior Publication Data
US 2015/0151298 A1    Jun. 4, 2015

Related U.S. Application Data

(60) Provisional application No. 61/996,969, filed on Oct. 22, 2013, provisional application No. 62/058,658, filed on Oct. 1, 2014.

(51) Int. Cl.
*B01L 3/00*    (2006.01)
*G01N 33/558*    (2006.01)

(52) U.S. Cl.
CPC ...... *B01L 3/502761* (2013.01); *G01N 33/558* (2013.01); *B01L 2200/0647* (2013.01);
(Continued)

(58) Field of Classification Search
None
See application file for complete search history.

(56) References Cited

U.S. PATENT DOCUMENTS 6,294,063 B1    9/2001    Becker
6,942,776 B2    9/2005    Medoro
(Continued)

FOREIGN PATENT DOCUMENTS

EP    1065378 A2    1/2001
JP    2005-521425    7/2005
(Continued)

OTHER PUBLICATIONS

Chiou et al., Massively Parallel Manipulation of Single Cells and Microparticles Using Optical Images, Nature 436:370-73 (2005).
(Continued)

*Primary Examiner* — Erik B Crawford
(74) *Attorney, Agent, or Firm* — Kenneth E. Horton; Kirton McConkie

(57) ABSTRACT

A microfluidic device can comprise at least one swept region that is fluidically connected to unswept regions. The fluidic connections between the swept region and the unswept regions can enable diffusion but substantially no flow of media between the swept region and the unswept regions. The capability of biological micro-objects to produce an analyte of interest can be assayed in such a microfluidic device. Biological micro-objects in sample material loaded into a microfluidic device can be selected for particular characteristics and disposed into unswept regions. The sample material can then be flowed out of the swept region and an assay material flowed into the swept region. Flows of medium in the swept region do not substantially affect the biological micro-objects in the unswept regions, but any analyte of interest produced by a biological micro-object can diffuse from an unswept region into the swept region, where the analyte can react with the assay material to produce a localized detectable reaction. Any such detected reactions
(Continued)

can be analyzed to determine which, if any, of the biological micro-objects are producers of the analyte of interest.

16 Claims, 23 Drawing Sheets

(52) U.S. Cl.
CPC ............... *B01L 2200/0652* (2013.01); *B01L 2200/0668* (2013.01); *B01L 2300/087* (2013.01); *B01L 2300/0816* (2013.01); *B01L 2300/0864* (2013.01); *B01L 2400/0424* (2013.01); *B01L 2400/0433* (2013.01); *B01L 2400/0454* (2013.01); *G01N 2469/20* (2013.01)

(56) References Cited

U.S. PATENT DOCUMENTS

| | | |
|---|---|---|
| 7,090,759 B1 | 8/2006 | Seul |
| 7,964,078 B2 | 6/2011 | Lee et al. |
| 2003/0008364 A1 | 1/2003 | Wang |
| 2003/0175947 A1* | 9/2003 | Liu .................... B01F 11/0071 435/288.5 |
| 2003/0224528 A1 | 12/2003 | Chiou |
| 2004/0072278 A1 | 4/2004 | Chou et al. |
| 2004/0191789 A1 | 9/2004 | Manaresi et al. |
| 2005/0112548 A1 | 5/2005 | Segawa |
| 2005/0129581 A1 | 6/2005 | McBride |
| 2005/0175981 A1 | 8/2005 | Voldman |
| 2006/0091015 A1 | 5/2006 | Lau |
| 2006/0154361 A1 | 7/2006 | Wikswo et al. |
| 2007/0095669 A1 | 5/2007 | Lau |
| 2007/0183934 A1 | 8/2007 | Diercks et al. |
| 2007/0240495 A1* | 10/2007 | Hirahara .......... B01L 3/502746 73/53.01 |
| 2007/0292941 A1 | 12/2007 | Handique |
| 2008/0302732 A1 | 12/2008 | Soh |
| 2009/0170186 A1 | 7/2009 | Wu |
| 2010/0003666 A1 | 1/2010 | Lee |
| 2010/0101960 A1 | 4/2010 | Ohta |
| 2010/0273681 A1 | 10/2010 | Cerrina et al. |
| 2013/0118905 A1 | 5/2013 | Morimoto |
| 2013/0130232 A1* | 5/2013 | Weibel .............. G01N 33/54386 435/5 |
| 2013/0190212 A1 | 7/2013 | Handique |
| 2013/0261021 A1* | 10/2013 | Bocchi .................. B01L 3/5088 506/9 |
| 2014/0124370 A1 | 5/2014 | Short et al. |
| 2015/0151307 A1 | 4/2015 | Breinlinger |
| 2015/0165436 A1 | 4/2015 | Chapman |
| 2015/0167043 A1* | 6/2015 | Goluch ..................... C12M 1/34 435/29 |
| 2016/0252495 A1 | 9/2016 | Ricicova et al. |

FOREIGN PATENT DOCUMENTS

| | | |
|---|---|---|
| WO | 2009130694 A2 | 10/2009 |
| WO | 2009146143 A2 | 12/2009 |
| WO | 201014078 | 12/2010 |
| WO | 2011160430 A1 | 12/2011 |
| WO | 2012037030 A2 | 3/2012 |
| WO | 2014070873 A1 | 5/2014 |

OTHER PUBLICATIONS

Yi et al., Microfluidics technology for manipulation and analysis of biological cells, Yi, Analytica Chimica Acta 560:1-23 (2006).
Fuchs et al., Electronic sorting and recovery of single live cells from microlitre sized samples, Fuchs, Lab on a Chip 6:121-26 (2006)
Nevill et al., Integrated Microfluidic Cell Culture and Lysis on a Chip, Lab on a Chip 7:1689-95 (2007).
Valley et al., Optoelectronic Tweezers as a Tool for Parallel Single-Cell Manipulation and Stimulation, IEEE Transactions on Biomedical Circuits and Systems 3(6):424-30 (2009).
Young et al., Fundamentals of Microfluidic Cell Culture in Controlled Microenvironments, Chem Soc Rev 39(3):1036-48 (2010).
International Search Report and Written Opinion for PCT Application Serial No. PCT/2014/061787 (dated Feb. 25, 2015), 11 pages.
Hur, Soojung Claire et al., High-Throughput Size-Based Rare Cell Enrichment Using Microscale Vortices, Biomicrofluidics, 2011, vol. 5(2), Article No. 022206 (internal pp. 1-10).
Iliescu, Ciprian et al., Continuous Field-Flow Separation of Particle Populations in a Dielectrophoretic Chip with Three Dimensional Electrodes, Applied Physics Letters, 2007, vol. 90, Article No. 234104 (internal pp. 1-3).
Xu, Guolin et al., Recent Trends in Dielectrophoresis Informacije MIDEM, 2010, Vo. 40, Issue No. 4, pp. 253-262.
Chen, Jian et al., Microfluidic Approaches for Cancer Cell Detection, Characterization, and Separation, Lab on a Chip, 2012. vol. 12, No. 10, pp. 1753-1767.
The International Bureau of WIPO International Report on Patentability for PCT/US2014/061837, dated May 6, 2016
European Patent Office, Supplemental Partial European Search Report for Application No. EP 14 85 5668, dated Sep. 28, 2016.
Somaweera H. et al., Generation of a Chemical Gradient Across an Array of 256 Cell Cultures in a Single Chip. Analyst., Oct. 7, 2013, vol. 138, No. 19, pp. 5566-5571.
Gasgoyne et al., Dielectrophoretic Separation of Cancer Cells from Blood, IEEE Trans. Industrial Appl., 670-678 (1997).
Chung et al., Imaging Single-Cell Signaling Dynamics With a Deterministic High-Density Single-Cell Trap Array, Anal. Chem. 83(18):7044-7052 (2011).
Japanese Patent Office, Notice of Reasons for Rejection for Application No. 2015-539940, dated Sep. 19, 2017.

\* cited by examiner

Figure 7B
Figure 7C

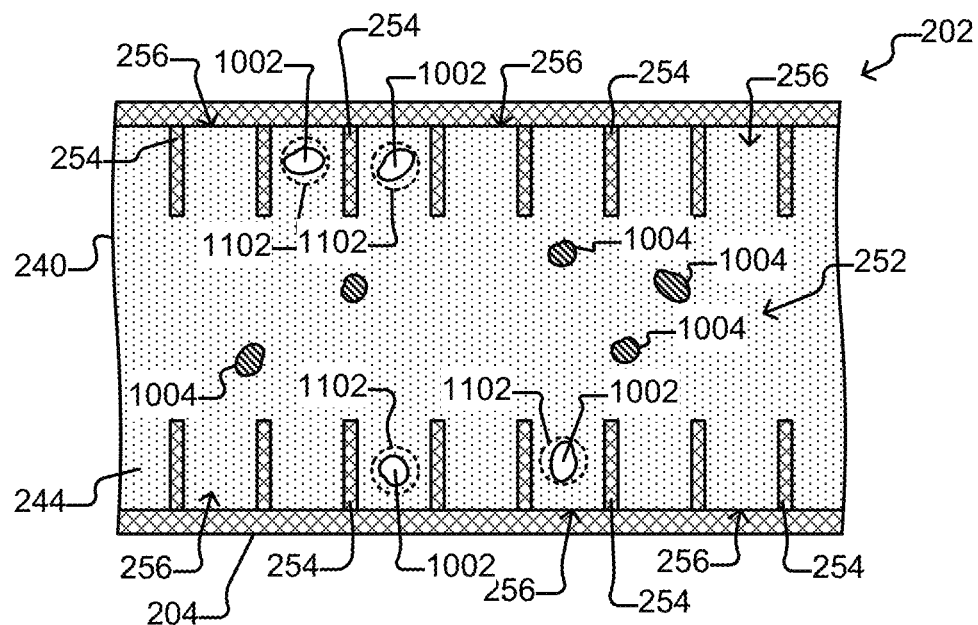
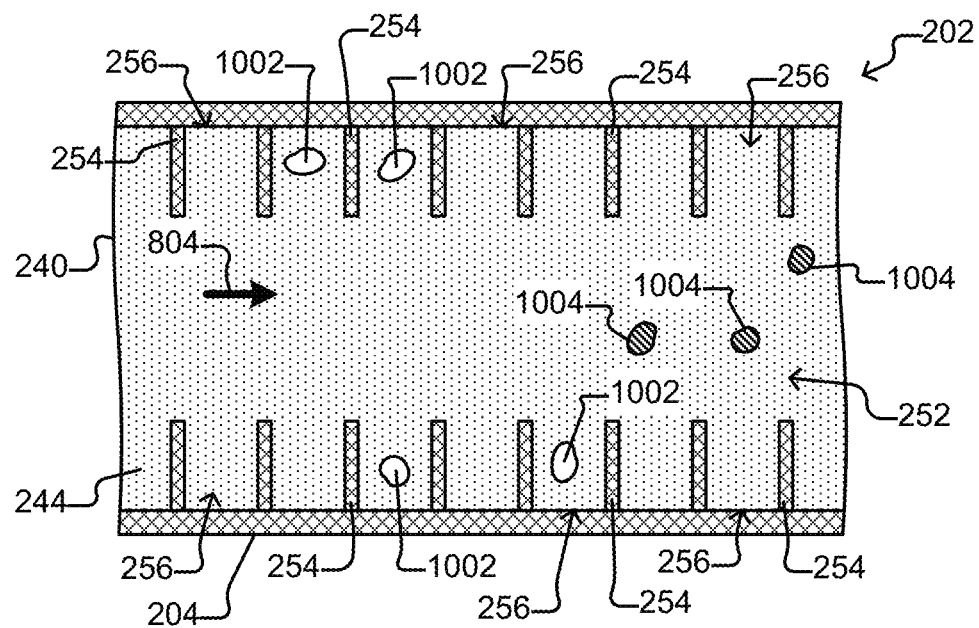

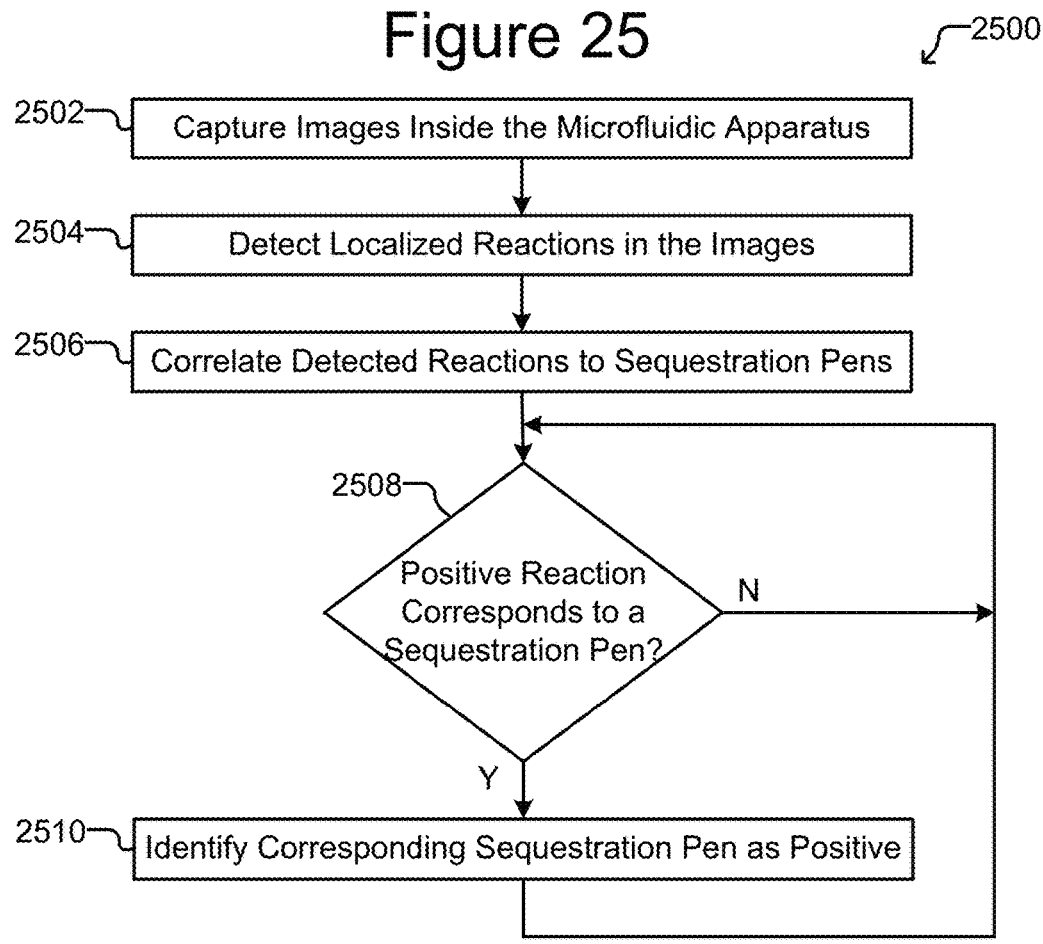
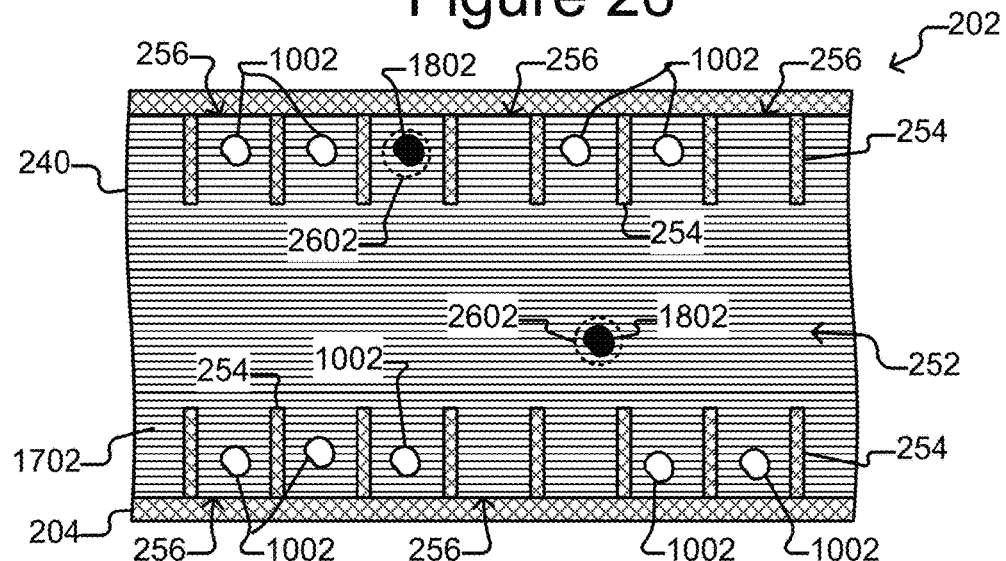

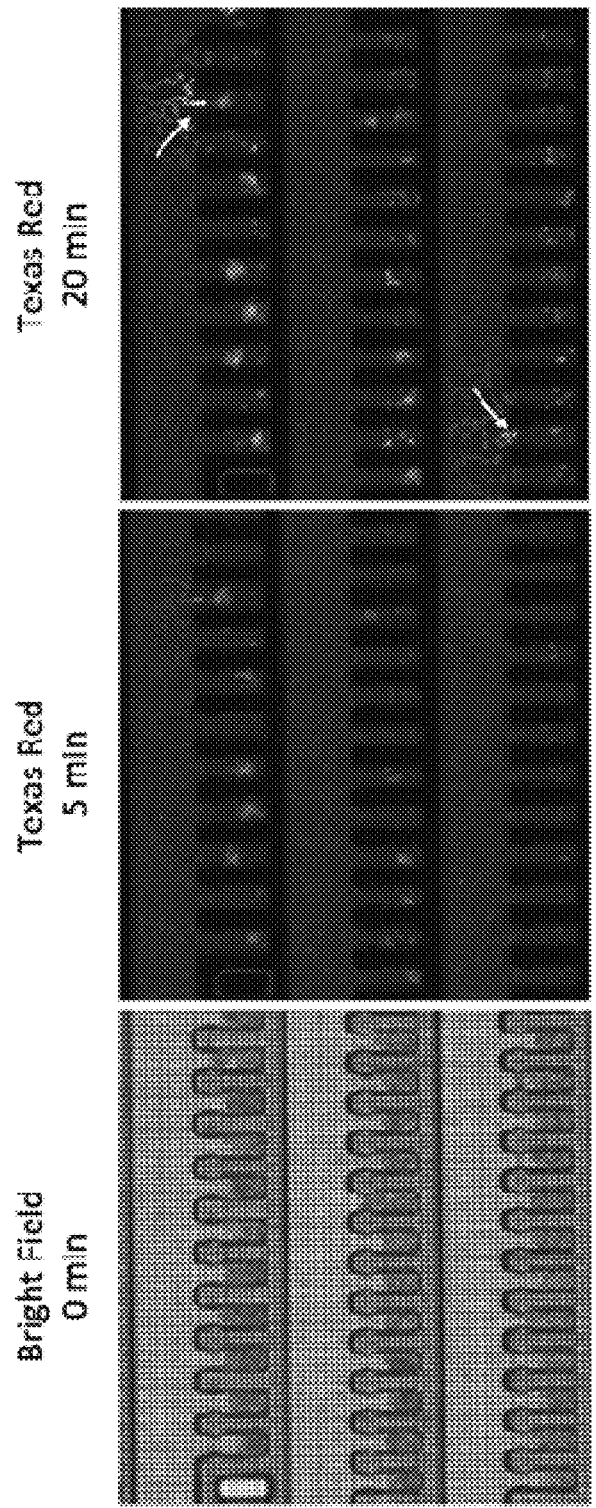

MICROFLUIDIC DEVICES HAVING ISOLATION PENS AND METHODS OF TESTING BIOLOGICAL MICRO-OBJECTS WITH SAME

CROSS REFERENCE TO RELATED APPLICATION(S)

This application is a non-provisional application and claims the benefit of U.S. provisional patent application Ser. No. 61/996,969, filed on Oct. 22, 2013 and claims the benefit of U.S. provisional patent application Ser. No. 62/058,658, filed on Oct. 1, 2014, each of which disclosures is herein incorporated by reference in its entirety.

BACKGROUND

As the field of microfluidics continues to progress, microfluidic devices have become convenient platforms for processing and manipulating micro-objects such as biological cells. Some embodiments of the present invention are directed to improvements in microfluidic devices and methods of operating microfluidic devices.

SUMMARY

In some embodiments of the invention, a microfluidic device can include a flow region and a microfluidic sequestration pen. The flow region can be configured to contain a flow of a first fluidic medium. The microfluidic sequestration pen can include an isolation structure and a connection region. The isolation structure can comprise an isolation region configured to contain a second fluidic medium. The connection region can fluidically connect the isolation region to the flow region so that, while the flow region and the microfluidic sequestration pen are substantially filled with fluidic media: components of the second medium are able to diffuse into the first medium or components of the first medium are able to diffuse into the second medium; and there is substantially no flow of the first medium from the flow region into the isolation region.

Some embodiments of the invention include a process of analyzing a biological micro-object in a microfluidic device, which can comprise a microfluidic channel to which at least one microfluidic sequestration pen is fluidically connected. The at least one sequestration pen can comprise a fluidic isolation structure comprising an isolation region and a connection region fluidically connecting the isolation region to the channel. The process can include loading one or more biological micro-objects into the at least one sequestration pen, and incubating the loaded biological micro-objects for a period of time sufficient to allow the biological micro-objects to produce an analyte of interest. The process can also include disposing capture micro-objects in the channel adjacent to an opening from the connection region of the at least one sequestration pen to the channel, and monitoring binding of the capture micro-objects to the analyte of interest. The capture micro-objects can comprise at least one type of affinity agent capable of specifically binding the analyte of interest.

BRIEF DESCRIPTION OF THE DRAWINGS

FIGS. 7A-7C show yet another example of a configuration of a sequestration pen according to some embodiments of the invention.

FIG. 13 illustrates an example of moving selected biological micro-objects into holding pens in the microfluidic device of FIGS. 2A-2C according to some embodiments of the invention.

FIG. 14 shows an example of flushing biological micro-objects from the flow path of the microfluidic device of FIGS. 2A-2C according to some embodiments of the invention.

FIG. 25 is a process that illustrates an example of detecting localized reactions and identifying sequestration pens containing positive biological micro-objects in a microfluidic device such as the device illustrated in FIGS. 4A-4C according to some embodiments of the invention.

FIG. 26 illustrates moving negative biological micro-objects from holding pens into the flow path in the device of FIGS. 2A-2C according to some embodiments of the invention.

FIGS. 31A-C depict a microfluidic device comprising a microchannel and a plurality of sequestration pens that open off of the microchannel. Each sequestration pen contains a plurality of mouse splenocytes. FIG. 31A is a bright field image of a portion of the microchannel device. FIGS. 31B and 31C are fluorescence images obtained using a Texas Red filter. In FIG. 31B, the image was obtained 5 minutes after the start of the antigen specificity assay described in Example 1. In FIG. 31C, the image was obtained 20 minutes after the start of the antigen specificity assay described in Example 1. The white arrows in FIG. 31C point to sequestration pens that generated a positive signal in the assay.

DETAILED DESCRIPTION OF EXEMPLARY EMBODIMENTS

Figure 1:
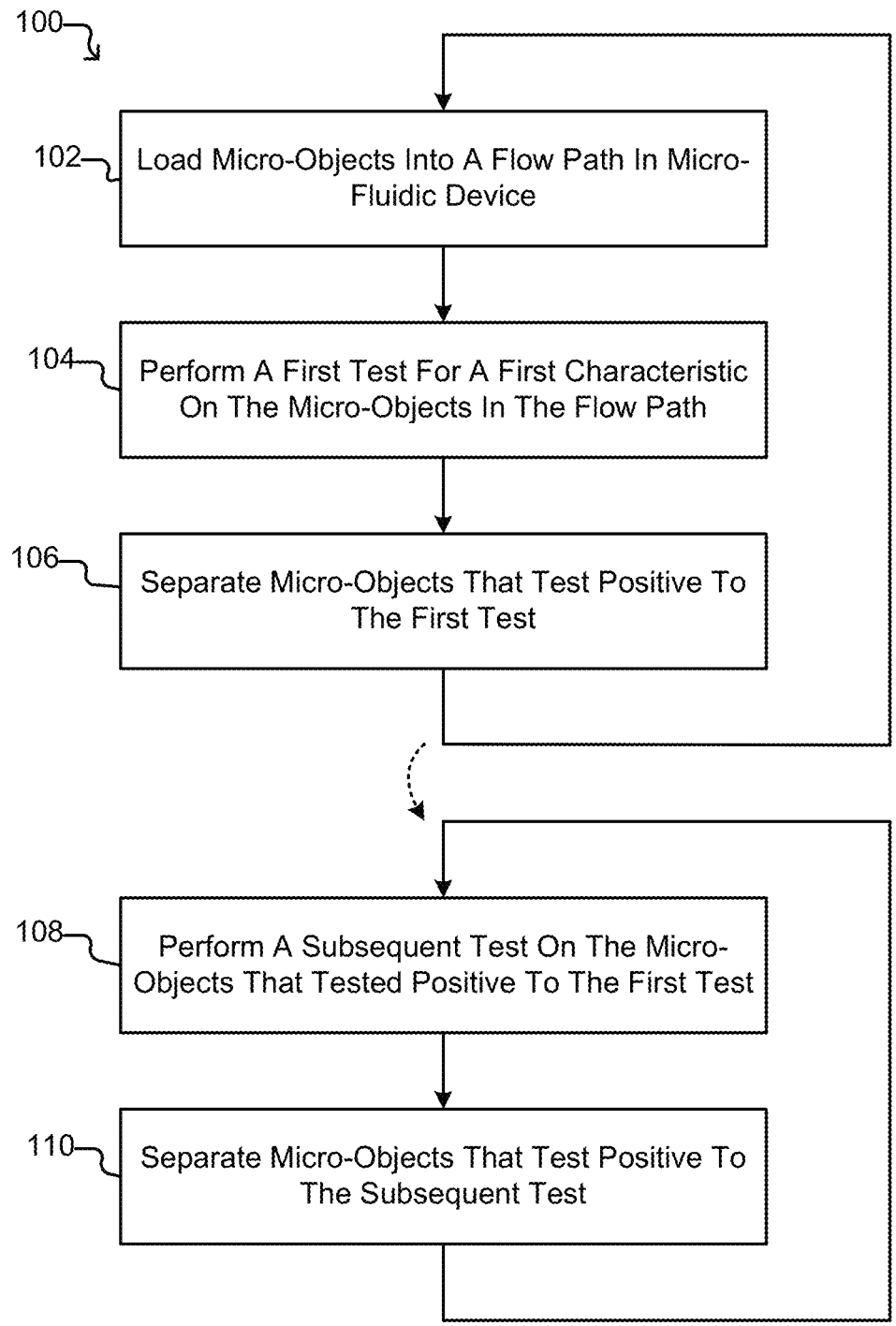
FIG. 1 is an example of a process in which at least two tests can be performed on micro-objects in a microfluidic device according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the Figures may show simplified or partial views, and the dimensions of elements in the Figures may be exaggerated or otherwise not in proportion for clarity. In addition, as the terms "on," "attached to," or "coupled to" are used herein, one element (e.g., a material, a layer, a substrate, etc.) can be "on," "attached to," or "coupled to" another element regardless of whether the one element is directly on, attached, or coupled to the other element or there are one or more intervening elements between the one element and the other element. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "ones" means more than one.

As used herein, the term "micro-object" can encompass one or more of the following: inanimate micro-objects such as microparticles, microbeads (e.g., polystyrene beads, Luminex™ beads, or the like), magnetic beads, microrods, microwires, quantum dots, and the like; biological micro-objects such as cells (e.g., embryos, oocytes, sperms, cells dissociated from a tissue, blood cells, hybridomas, cultured cells, cells from a cell line, cancer cells, infected cells, transfected and/or transformed cells, reporter cells, and the like), liposomes (e.g, synthetic or derived from membrane preparations), lipid nanorafts, and the like; or a combination of inanimate micro-objects and biological micro-objects (e.g., microbeads attached to cells, liposome-coated microbeads, liposome-coated magnetic beads, or the like). Lipid nanorafts have been described, e.g., in Ritchie et al. (2009) "Reconstitution of Membrane Proteins in Phospholipid Bilayer Nanodiscs," Methods Enzymol., 464:211-231.

As used herein, the term "cell" refers to a biological cell, which can be a plant cell, an animal cell (e.g., a mammalian cell), a bacterial cell, a fungal cell, or the like. An animal cell can be, for example, from a human, a mouse, a rat, a horse, a goat, a sheep, a cow, a primate, or the like.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

In some embodiments, a microfluidic device can comprise "swept" regions and "unswept" regions. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region.

The capability of biological micro-objects (e.g., biological cells) to produce specific biological materials can be assayed in such a microfluidic device. For example, sample material comprising biological micro-objects to be assayed for production of an analyte of interest can be loaded into a swept region of the microfluidic device. Ones of the biological micro-objects can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Figure 2A:
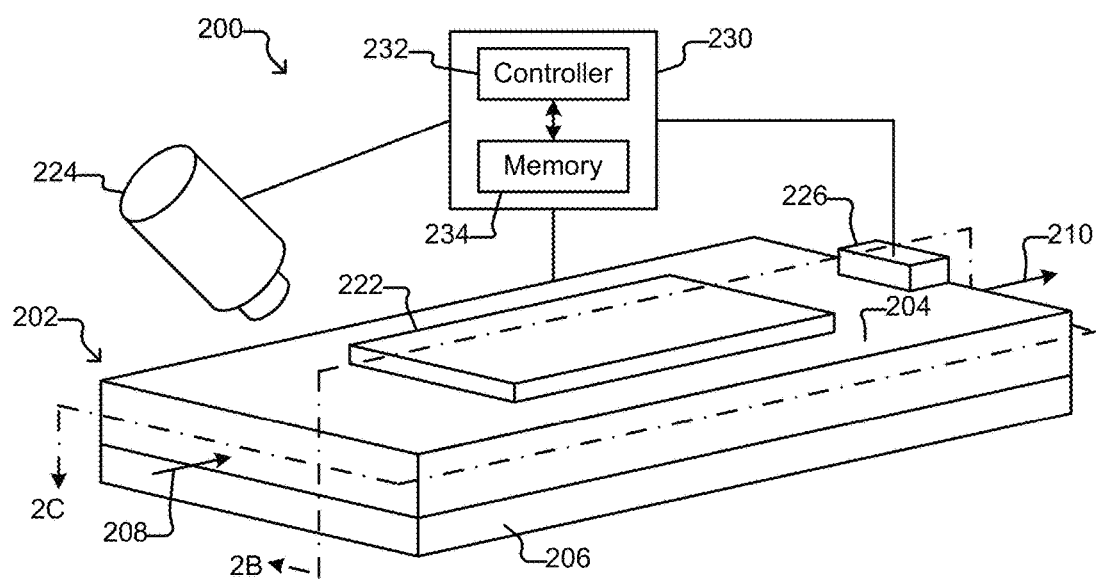
FIG. 2A is a perspective view of a microfluidic device with which the process of FIG. 1 can be performed according to some embodiments of the invention.
Figure 2B:
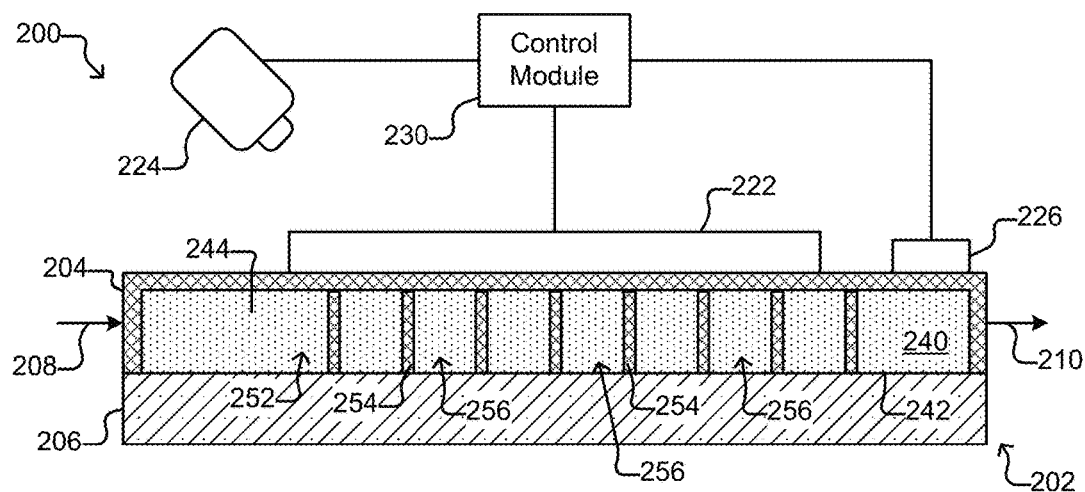
FIG. 2B is a side, cross-sectional view of the microfluidic device of FIG. 2A.
Figure 2C:
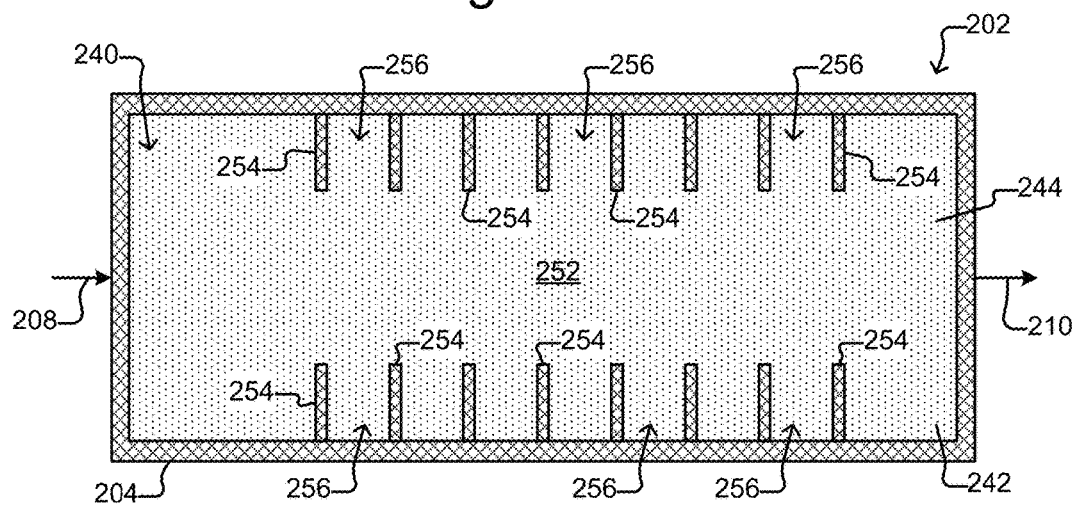
FIG. 2C is a top, cross-sectional view of the microfluidic device of FIG. 2A.
Figure 3A:
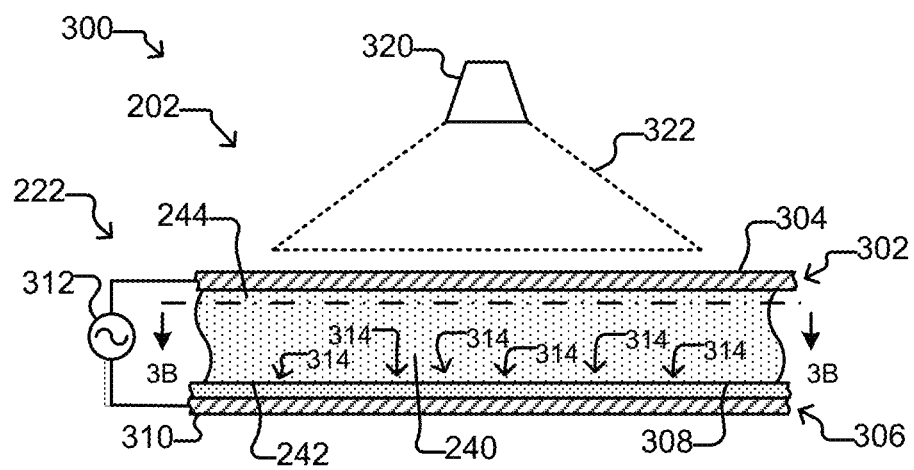
FIG. 3A is a partial side, cross-sectional view of the microfluidic device of FIGS. 2A-2C absent the barriers (for ease of illustration) in which the selector is configured as a dielectrophoresis (DEP) device according to some embodiments of the invention.
Figure 3B:
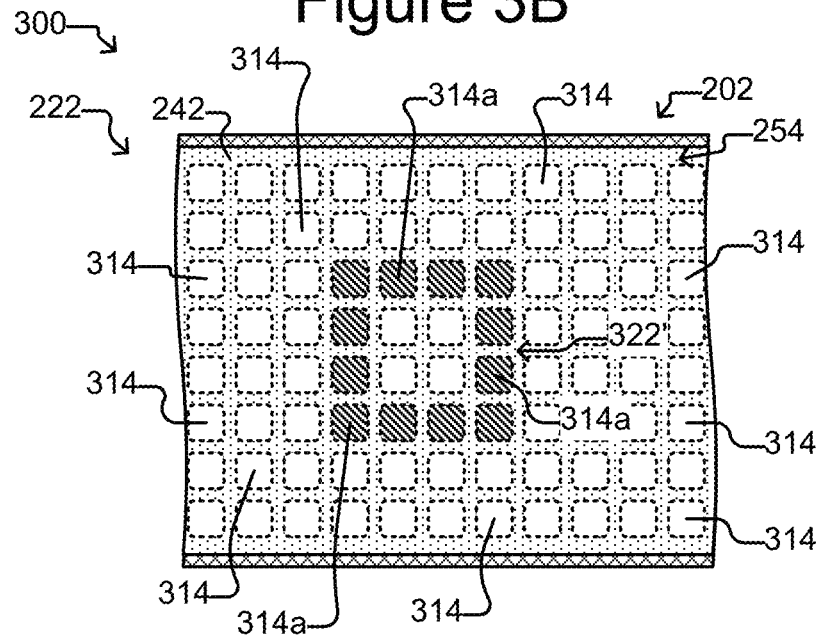
FIG. 3B is a partial top, cross-section view of FIG. 3A.
Figure 4A:
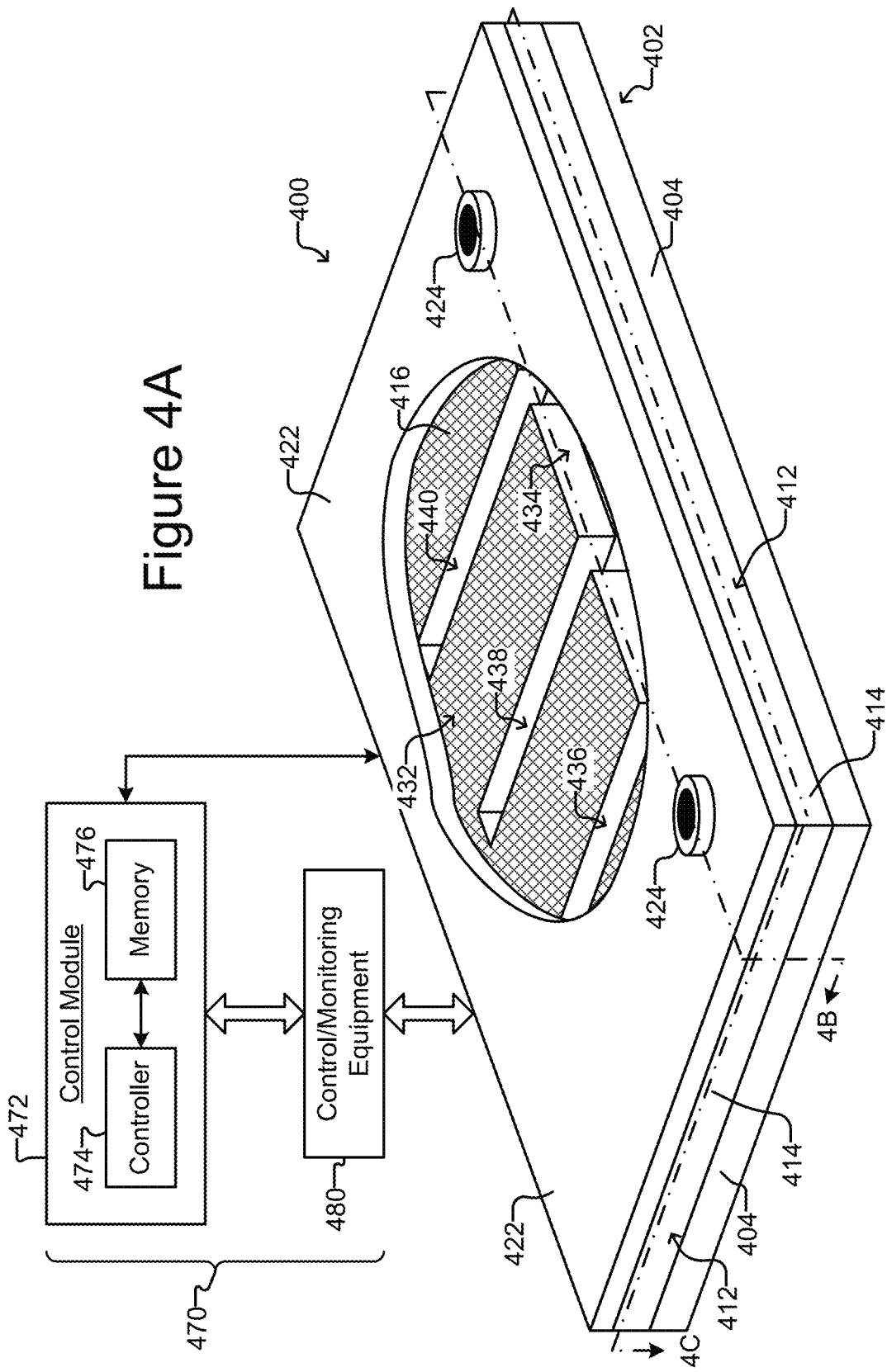
FIG. 4A is a perspective view of another example of a microfluidic device according to some embodiments of the invention.
Figure 4B:
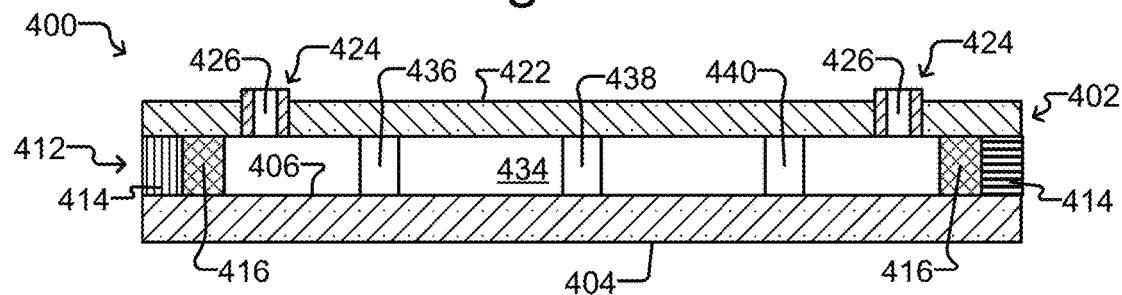
FIG. 4B is a side, cross-sectional view of the microfluidic device of FIG. 4A.
Figure 4C:
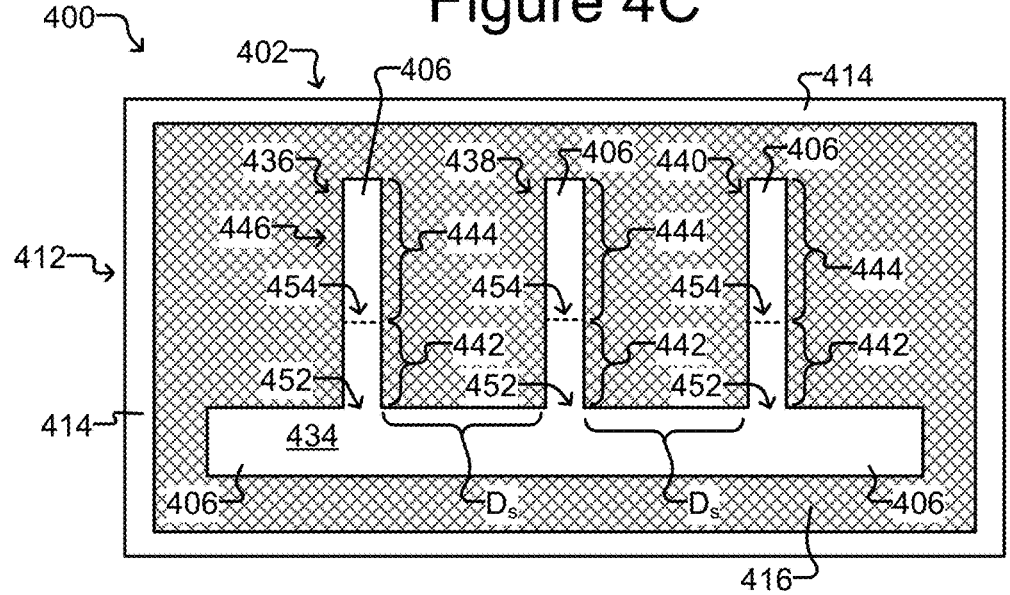
FIG. 4C is a top, cross-sectional view of the microfluidic device of FIG. 4A.

FIG. 1 illustrates an example of a process 100 for testing micro-objects in a microfluidic device according to some embodiments of the invention. FIGS. 2A-2C illustrate an example of a microfluidic device 200 with which the process 100 can be performed, and FIGS. 3A and 3B illustrate an example of a dielectrophoresis (DEP) device that can be part of the microfluidic device 200. FIGS. 4A-4C illustrate another example of a microfluidic device 400 with which the process 100 can also be performed. Neither the device 200 of FIGS. 2A-2C nor the device 400 of FIGS. 4A-4C, however, is limited to performing the process 100 of FIG. 1. Nor is the process 100 limited to being performed on the device 200 or 400.

As shown in FIG. 1, the process 100 can load a mixture of micro-objects into a flow path in a microfluidic device at step 102. The mixture loaded at step 102 can comprise micro-objects of different types as well as debris and other objects. At step 104, the process 100 can test the micro-objects in the flow path for a first characteristic, and at step 106, the process 100 can separate micro-objects that test positive for the first characteristic from micro-objects that do not test positive (e.g., micro-objects that test negative) for the first characteristic. As shown, the process 100 can repeat steps 102-106 any number of times. For example, steps 102-106 can be performed k times, after which k mixtures of micro-objects have been loaded at step 102 and sorted at steps 104, 106 into an initial group of micro-objects all of which tested positive for the first characteristic. The number k can be any integer that is one or greater. (Hereinafter, biological micro-objects that test positive to a test are sometimes referred to as "positive" biological micro-objects, and biological micro-objects that do not test positive to the test (e.g., test negative to the test) are sometimes referred to as "negative" biological micro-objects.)

The process 100 can then proceed to step 108, where the process 100 can perform a subsequent test on the initial group of micro-objects. The subsequent test performed at step 108 can be different than the first test performed at step 104. For example, the subsequent test can test for a subsequent characteristic that is different than the first characteristic tested at step 104. As another example, the subsequent test performed at step 108 can test for the same characteristic as step 104 (the first characteristic mentioned above), but the subsequent test can have a different sensitivity, accuracy, precision, or the like. For example, the subsequent test performed at step 108 can be more sensitive to the first characteristic than the first test performed at step 104. Regardless, at step 110, the process 100 can separate the micro-objects that test positive to the subsequent test at step 108 from the micro-objects that test negative to the subsequent test.

If the first test of step 104 and the subsequent test of step 108 test for the same characteristic, after steps 108 and 110, micro-objects that tested positive for that characteristic (the first characteristic referred to above in the discussion of step 104) in response to two different tests have been separated from the k mixtures of micro-objects loaded into the microfluidic device at k performances of step 102. As shown, steps 108 and 110 can be repeated, and at each repetition, the process 100 can apply a different subsequent test at step 108 that tests for the same characteristic. Indeed, steps 108 and 110 can be repeated n times after which the process 100 has sorted from the k mixtures of micro-objects loaded into the microfluidic device at step 102 micro-objects that have tested positive n+1 times for the first characteristic tested at steps 104 and 108. The number n can be any integer that is one or greater.

As noted, the process 100 can alternatively test at step 108 for a subsequent characteristic that is different than the first characteristic tested at step 104. In such an embodiment, micro-objects having both the first characteristic and the subsequent characteristic have been sorted from the k mixtures of micro-objects loaded into the microfluidic device at step 102. If steps 108 and 110 are repeated, at each repetition, the process 100 can test for a different subsequent characteristic at step 108. For example, at each performance of step 108, the process 100 can test for a subsequent characteristic that is not only different than the first characteristic but also different than any preceding subsequent characteristic tested during any previous pass through steps 108 and 110. At each performance of step 110, the process 100 can separate the micro-objects that test positive for the subsequent characteristic at step 108.

As noted, steps 108 and 110 can be repeated n times. After performing steps 108 and 110 $n$ times, the process 100 has sorted from the k mixtures of micro-objects loaded into the microfluidic device at step 102 micro-objects that have all n+1 of the characteristics tested at steps 104 and 108. The number n can be an integer that is one or greater.

Variations of the process 100 are contemplated. For example, in some embodiments, the repetition of step 108 can sometimes test for a new characteristic not tested at step 104 or any previous performance of step 108 and other times test for the same characteristic tested at step 104 or a previous performance of step 108. As another example, at step 106 or any repetition of step 110, the process 100 can separate the micro-objects that tested negative from the micro-objects that tested positive. As yet another example, the process 100 can repeat step 104 multiple times before proceeding to step 106. In such an example, the process 100 can test for different characteristics at each repetition of step 104 and then separate the micro-objects that tested positive at each repetition of step 104 from micro-objects that tested negative to at least one repetition of step 104. Likewise, step 108 can be repeated multiple times before proceeding to step 110.

Examples of microfluidic devices 200 and 400 are now discussed with respect to FIGS. 2A-7C. Examples of operation of the process 100 with the devices 200 and 400 in which the micro-objects include biological micro-objects such as biological cells are then described with respect to FIGS. 8-30.

FIGS. 2A-2C illustrate an example of a microfluidic device 200 with which the process 100 can be performed. As shown, the microfluidic device 200 can comprise a housing 202, a selector 222, a detector 224, a flow controller 226, and a control module 230.

As shown, the housing 202 can comprise one or more flow regions 240 for holding a liquid medium 244. FIG. 2B illustrates an inner surface 242 of the flow region 240 on which the medium 244 can be disposed as even (e.g., flat) and featureless. The inner surface 242, however, can alternatively be uneven (e.g., not flat) and comprise features such as electric terminals (not shown).

The housing 202 can comprise one or more inlets 208 through which the medium 244 can be input into the flow region 240. An inlet 208 can be, for example, an input port, an opening, a valve, another channel, fluidic connectors, or the like. The housing 202 can also comprise one or more outlets 210 through which the medium 244 can be removed. An outlet 210 can be, for example, an output port, an opening, a valve, a channel, fluidic connectors, or the like. As another example, the outlet 210 can comprise a droplet outputting mechanism such as any of the outputting mechanisms disclosed in U.S. patent application Ser. No. 13/856,781 filed Apr. 4, 2013. All or part of the housing 202 can be gas permeable to allow gas (e.g., ambient air) to enter and exit the flow region 240.

The housing 202 can also comprise a microfluidic structure 204 disposed on a base (e.g., a substrate) 206. The microfluidic structure 204 can comprise a flexible material, such as rubber, plastic, an elastomer, silicone (e.g., patternable silicone), polydimethylsiloxane ("PDMS"), or the like, which can be gas permeable. Alternatively, the microfluidic structure 204 can comprise other materials including rigid materials. The base 206 can comprise one or more substrates. Although illustrated as a single structure, the base 206 can comprise multiple interconnected structures such as multiple substrates. The micro-fluidic structure 204 can likewise comprise multiple structures, which can be interconnected. For example, the micro-fluidic structure 204 can additionally comprise a cover (not shown) made from material that is the same as or different than the other material in the structure.

The microfluidic structure 204 and the base 206 can define the flow region 240. Although one flow region 240 is shown in FIGS. 2A-2C, the microfluidic structure 204 and the base 206 can define multiple flow regions for the medium 244. The flow region 240 can comprise channels (252 in FIG. 2C) and chambers, which can be interconnected to form microfluidic circuits. For enclosures that comprise more than one flow region 240, each flow region 240 can be associated with one or more inlets 108 and one or more outlets 110 for respectively inputting and removing medium 244 from the flow region 240.

As shown FIGS. 2B and 2C, the flow region 240 can comprise one or more channels 252 for the medium 244. For example, the channel 252 can be generally from the inlet 208 to the outlet 210. As also shown, holding pens 256 defining non-flow spaces (or isolation regions) can be disposed in the flow region 240. That is, at least a portion of the interior of each holding pen 256 can be a non-flow space into which medium 244 from the channel 252 does not directly flow except when an empty flow region 240 is initially being filled with the medium 244. For example, each holding pen 256 can comprise one or more barriers 254 that form a partial enclosure the inside of which can include a non-flow space. The barriers 254 that define the holding pens 256 can thus prevent medium 244 from flowing directly into the protected interior of any of the holding pens 256 from the channel 252 while the flow region 240 is filled with medium 244. For example, a barrier 254 of a pen 256 can substantially prevent bulk flow of the medium 244 from the channel 252 into the non-flow spaces of the pens 256 while the flow region 240 is filled with medium 244, instead allowing substantially only diffusive mixing of medium from the channel 252 with medium in the non-flow space in a pen 256. Accordingly, exchange of nutrients and waste between the non-flow space in a holding pen 256 and the channel 252 can occur substantially only by diffusion.

The foregoing can be accomplished by orienting a pen 256 such that no opening into the pen 256 faces directly into the flow of medium 244 in a channel 252. For example, if the flow of medium is from the inlet 208 to the outlet 210 (and thus left to right) in the channel 252 in FIG. 2C, each of the pens 256 substantially impedes direct flow of medium 244 from the channel 252 into the pens 256 because the openings of each of the pens 256 do not face to the left in FIG. 2C, which would be directly into such a flow.

There can be many such holding pens 256 in the flow region 240 disposed in any pattern, and the holding pens 256 can be any of many different sizes and shapes. Although shown as disposed against side walls of the microfluidic structure 204 in FIG. 2C, one or more (including all) of the pens 256 can be stand alone structures disposed away from a sidewall of the microfluidic structure 204 in the channel 252. As shown in FIG. 2C, openings of the holding pens 256 can be disposed adjacent to the channel 252, which can be adjacent to the openings of more than one pen 256. Although one channel 252 adjacent to the fourteen pens 256 is shown, there can be more channels 252, and there can be more or fewer pens 256 adjacent to any particular channel 252.

The barriers 254 of the pens 256 can comprise any of the types of materials discussed above with respect to the microfluidic structure 204. The barriers 254 can comprise the same material as the microfluidic structure 204 or a different material. The barriers 254 can extend from the surface 242 of the base 206 across the entirety of the flow region 240 to an upper wall (opposite the surface 242) of the microfluidic structure 204 as shown in FIG. 2B. Alternatively, one or more of the barriers 254 can extend only partially across the flow region 240 and thus not extend entirely to the surface 242 or the upper wall of the microfluidic structure 204.

The selector 222 can be configured to create selectively electrokinetic forces on micro-objects (not shown) in the medium 244. For example, the selector 222 can be configured to selectively activate (e.g., turn on) and deactivate (e.g., turn off) electrodes at the inner surface 242 of the flow region 240. The electrodes can create forces in the medium 244 that attract or repel micro-objects (not shown) in the medium 244, and the selector 222 can thus select and move one or more micro-objects in the medium 244. The electrodes can be, for example, dielectrophoresis (DEP) electrodes.

For example, the selector 222 can comprise one or more optical (e.g., laser) tweezers devices and/or one or more optoelectronic tweezers (OET) devices (e.g., as disclosed in U.S. Pat. No. 7,612,355 (which is incorporated in its entirety by reference herein) or U.S. patent application Ser. No. 14/051,004 (which is also incorporated in its entirety by reference herein). As yet another example, the selector 222 can include one or more devices (not shown) for moving a droplet of the medium 244 in which one or more of micro-objects are suspended. Such devices (not shown) can include electrowetting devices such as optoelectronic wetting (OEW) devices (e.g., as disclosed in U.S. Pat. No. 6,958,132). The selector 222 can thus be characterized as a DEP device in some embodiments.

FIGS. 3A and 3B illustrate an example in which the selector 222 comprises a DEP device 300. As shown, the DEP device 300 can comprise a first electrode 304, a second electrode 310, an electrode activation substrate 308, a power source 312 (e.g., an alternating current (AC) power source), and a light source 320. Medium 244 in the flow region 240 and the electrode activation substrate 308 can separate the electrodes 304, 310. Changing patterns of light 322 from the light source 320 can selectively activate and deactivate changing patterns of DEP electrodes at regions 314 of the inner surface 242 of the flow region 240. (Hereinafter the regions 314 are referred to as "electrode regions.")

In the example illustrated in FIG. 3B, a light pattern 322' directed onto the inner surface 242 illuminates the cross-hatched electrode regions 314a in the square pattern shown. The other electrode regions 314 are not illuminated and are hereinafter referred to as "dark" electrode regions 314. The relative electrical impedance across the electrode activation substrate 308 from each dark electrode region 314 to the second electrode 310 is greater than the relative impedance from the first electrode 304 across the medium 244 in the flow region 240 to the dark electrode region 314. Illuminating an electrode region 314a, however, reduces the relative impedance across the electrode activation substrate 308 from the illuminated electrode region 314a to the second electrode 310 to less than the relative impedance from the first electrode 304 across the medium 244 in the flow region 240 to the illuminated electrode region 314a.

With the power source 312 activated, the foregoing creates an electric field gradient in the medium 244 between illuminated electrode regions 314a and adjacent dark electrode regions 314, which in turn creates local DEP forces that attract or repel nearby micro-objects (not shown) in the medium 244. DEP electrodes that attract or repel micro-objects in the medium 244 can thus be selectively activated and deactivated at many different such electrode regions 314 at the inner surface 242 of the flow region 240 by changing light patterns 322 projected form a light source 320 (e.g., a laser source or other type of light source) into the microfluidic device 200. Whether the DEP forces attract or repel nearby micro-objects can depend on such parameters as the frequency of the power source 312 and the dielectric properties of the medium 244 and/or micro-objects (not shown).

The square pattern 322' of illuminated electrode regions 314a illustrated in FIG. 3B is an example only. Any pattern of the electrode regions 314 can be illuminated by the pattern of light 322 projected into the device 200, and the pattern of illuminated electrode regions 322' can be repeatedly changed by changing the light pattern 322.

In some embodiments, the electrode activation substrate 308 can be a photoconductive material, and the inner surface 242 can be featureless. In such embodiments, the DEP electrodes 314 can be created anywhere and in any pattern on the inner surface 242 of the flow region 240 in accordance with the light pattern 322 (see FIG. 3A). The number and pattern of the electrode regions 314 are thus not fixed but correspond to the light pattern 322. Examples are illustrated in the aforementioned U.S. Pat. No. 7,612,355, in which the un-doped amorphous silicon material 24 shown in the drawings of the foregoing patent can be an example of photoconductive material that can compose the electrode activation substrate 308.

In other embodiments, the electrode activation substrate 308 can comprise a circuit substrate such as a semiconductor material comprising a plurality of doped layers, electrically insulating layers, and electrically conductive layers that form semiconductor integrated circuits such as is known in semiconductor fields. In such embodiments, electric circuit elements can form electrical connections between the electrode regions 314 at the inner surface 242 of the flow region 240 and the second electrode 310 that can be selectively activated and deactivated by the light pattern 322. When not activated, each electrical connection can have high impedance such that the relative impedance from a corresponding electrode region 314 to the second electrode 310 is greater than the relative impedance from the first electrode 304 through the medium 244 to the corresponding electrode region 314. When activated by light in the light pattern 322, however, each electrical connection can have low impedance such that the relative impedance from a corresponding electrode region 314 to the second electrode 310 is less than the relative impedance from the first electrode 304 through the medium 244 to the corresponding electrode region 314, which activates a DEP electrode at the corresponding electrode region 314 as discussed above. DEP electrodes that attract or repel micro-objects (not shown) in the medium 244 can thus be selectively activated and deactivated at many different electrode regions 314 at the inner surface 242 of the flow region 240 by the light pattern 322. Non-limiting examples of such configurations of the electrode activation substrate 308 include the phototransistor-based device 300 illustrated in FIGS. 21 and 22 of U.S. Pat. No. 7,956,339 and the devices 200, 400, 500, and 600 illustrated throughout the drawings in the aforementioned U.S. patent application Ser. No. 14/051,004.

In some embodiments, the first electrode 304 can be part of a first wall 302 (or cover) of the housing 202, and the electrode activation substrate 308 and second electrode 310 can be part of a second wall 306 (or base) of the housing 202, generally as illustrated in FIG. 3A. As shown, the flow region 240 can be between the first wall 302 and the second wall 306. The foregoing, however, is but an example. In other embodiments, the first electrode 304 can be part of the second wall 306 and one or both of the electrode activation substrate 308 and/or the second electrode 310 can be part of the first wall 302. As another example, the first electrode 304 can be part of the same wall 302 or 306 as the electrode activation substrate 308 and the second electrode 310. For example, the electrode activation substrate 308 can comprise the first electrode 304 and/or the second electrode 310. Moreover, the light source 320 can alternatively be located below the housing 202.

Configured as the DEP device 300 of FIGS. 3A and 3B, the selector 222 can thus select a micro-object (not shown) in the medium 244 in the flow region 240 by projecting a light pattern 322 into the device 200 to activate one or more DEP electrodes at electrode regions 314 of the inner surface 242 of the flow region 240 in a pattern that surrounds and captures the micro-object. The selector 222 can then move the captured micro-object by moving the light pattern 322 relative to the device 200. Alternatively, the device 200 can be moved relative to the light pattern 322.

Although the barriers 254 that define the holding pens 256 are illustrated in FIGS. 2B and 2C and discussed above as physical barriers, the barriers 254 can alternatively be virtual barriers comprising DEP forces activated by light in the light pattern 322.

With reference again to FIGS. 2A-2C, the detector 224 can be a mechanism for detecting events in the flow region 240. For example, the detector 224 can comprise a photodetector capable of detecting one or more radiation characteristics (e.g., due to fluorescence or luminescence) of a micro-object (not shown) in the medium. Such a detector 224 can be configured to detect, for example, that one or more micro-objects (not shown) in the medium 244 are radiating electromagnetic radiation and/or the approximate wavelength, brightness, intensity, or the like of the radiation. Examples of suitable photodetectors include without limitation photomultiplier tube detectors and avalanche photodetectors.

The detector 224 can alternatively or in addition comprise an imaging device for capturing digital images of the flow region 240 including micro-objects (not shown) in the medium 244. Examples of suitable imaging devices that the detector 224 can comprise include digital cameras or photosensors such as charge coupled devices and complementary metal-oxide-semiconductor imagers. Images can be captured with such devices and analyzed (e.g., by the control module 230 and/or a human operator).

The flow controller 226 can be configured to control a flow of the medium 244 in the flow region 240. For example, the flow controller 226 can control the direction and/or velocity of the flow. Non-limiting examples of the flow controller 226 include one or more pumps or fluid actuators. In some embodiments, the flow controller 226 can include additional elements such as one or more sensors (not shown) for sensing, for example, the velocity of the flow of the medium 244 in the flow region 240.

The control module 230 can be configured to receive signals from and control the selector 222, the detector 224, and/or the flow controller 226. As shown, the control module 230 can comprise a controller 232 and a memory 234. In some embodiments, the controller 232 can be a digital electronic controller (e.g., a microprocessor, microcontroller, computer, or the like) configured to operate in accordance with machine readable instructions (e.g., software, firmware, microcode, or the like) stored as non-transitory signals in the memory 234, which can be a digital electronic, optical, or magnetic memory device. Alternatively, the controller 232 can comprise hardwired digital circuitry and/or analog circuitry or a combination of a digital electronic controller operating in accordance with machine readable instructions and hardwired digital circuitry and/or analog circuitry. The controller 232 can be configured to perform all or any part of the processes 100, 2500 disclosed herein.

In some embodiments, the pens 256 can be shielded from illumination (e.g., by the detector 224 and/or the selector 222) or can be only selectively illuminated for brief periods of time. Biological micro-objects can thus be protected from further illumination or further illumination of the biological micro-objects can be minimized after the biological micro-objects are moved into the pens 256.

FIGS. 4A-4C illustrate another example of a microfluidic device 400. As shown, the microfluidic device 400 can enclose a microfluidic circuit 432 comprising a plurality of interconnected fluidic circuit elements. In the example illustrated in FIGS. 4A-4C, the microfluidic circuit 432 includes a flow region/channel 434 to which sequestration pens 436, 438, 440 are fluidically connected. One channel 434 and three sequestration pens 436, 438, 440 are shown, but there can be more than one channel 434 and more or fewer than three sequestration pens 436, 438, 440 connected with any particular channel. The channel 434 and sequestration pens 436, 438, 440 are examples of fluidic circuit elements. The microfluidic circuit 432 can also include additional or different fluidic circuit elements such as fluidic chambers, reservoirs, and the like.

Each sequestration pen 436, 438, 440 can comprise an isolation structure 446 defining an isolation region 444 and a connection region 442 fluidically connecting the isolation region 444 to the channel 434 (See FIG. 4C). The connection region 442 can comprise a proximal opening 452 to the channel 434 and a distal opening 454 to the isolation region 444. The connection region 442 can be configured so that a maximum penetration depth of a flow of a fluidic medium (not shown) flowing at a maximum velocity ($V_{max}$) in the channel 434 does not extend into the isolation region 444. A micro-object (not shown) or other material (not shown) disposed in an isolation region 444 of a pen 436, 438, 440 can thus be isolated from and not substantially affected by a flow of medium (not shown) in the channel 434. The channel 434 can thus be an example of a swept region, and the isolation regions of the sequestration pens 436, 438, 440 can be examples of unswept regions. Before turning to a more detailed discussion of the foregoing, a brief description of the microfluidic device 400 and examples of an associated control system 470 is provided.

The microfluidic device 400 can comprise an enclosure 402 enclosing the microfluidic circuit 432, which can contain one or more fluidic media. Although the device 400 can be physically structured in different ways, in the example shown in FIGS. 4A-4C, the enclosure 402 is depicted as comprising a support structure 404 (e.g., a base), a microfluidic circuit structure 412, and a cover 422. The support structure 404, microfluidic circuit structure 412, and the cover 422 can be attached to each other. For example, the microfluidic circuit structure 412 can be disposed on the support structure 404, and the cover 422 can be disposed over the microfluidic circuit structure 412. With the support structure 404 and the cover 422, the microfluidic circuit structure 412 can define the microfluidic circuit 432. An inner surface of the microfluidic circuit 432 is identified in the figures as 406.

The support structure 404 can be at the bottom and the cover 422 at the top of the device 400 as illustrated in FIGS. 4A and 4B. Alternatively, the support structure 404 and cover 422 can be in other orientations. For example, the support structure 404 can be at the top and the cover 422 at the bottom of the device 400. Regardless, there can be one or more ports 424 each comprising a passage 426 into or out of the enclosure 402. Examples of a passage 426 include a valve, a gate, a pass-through hole, or the like. Two ports 424 are shown but the device 400 can have only one or more than two.

The microfluidic circuit structure 412 can define circuit elements of the microfluidic circuit 432 or circuits in the enclosure 402. In the example, illustrated in FIGS. 4A-4C, the microfluidic circuit structure 412 comprises a frame 414 and a microfluidic circuit material 416.

The support structure 404 can comprise a substrate or a plurality of interconnected substrates. For example, the support structure 404 can comprise one or more interconnected semiconductor substrates, printed circuit boards, or the like. The frame 414 can partially or completely enclose the microfluidic circuit material 416. The frame 414 can be, for example, a relatively rigid structure substantially surrounding the microfluidic circuit material 416. For example the frame 414 can comprise a metal material.

The microfluidic circuit material 416 can be patterned with cavities or the like to define microfluidic circuit elements and interconnections of the microfluidic circuit 432. The microfluidic circuit material 416 can comprise a flexible material, such as rubber, plastic, elastomer, silicone (e.g., patternable silicone), PDMS, or the like, which can be gas permeable. Other examples of materials that can compose microfluidic circuit material 416 include molded glass, an etchable material such as silicon, photo-resist (e.g., SU8), or the like. In some embodiments, such materials—and thus the microfluidic circuit material 416—can be rigid and/or substantially impermeable to gas. Regardless, microfluidic circuit material 416 can be disposed on the support structure 404 and inside the frame 414.

The cover 422 can be an integral part of the frame 414 and/or the microfluidic circuit material 416. Alternatively, the cover 422 can be a structurally distinct element (as illustrated in FIGS. 4A and 4B). The cover 422 can comprise the same or different materials than the frame 414 and/or the microfluidic circuit material 416. Similarly, the support structure 404 can be a separate structure from the frame 414 or microfluidic circuit material 416 as illustrated or an integral part of the frame 414 or microfluidic circuit material 416. Likewise the frame 414 and microfluidic circuit material 416 can be separate structures as shown in FIGS. 4A-4C or integral portions of the same structure. In some embodiments, the cover 422 and/or the support structure 404 can be transparent to light.

FIG. 4A also illustrates simplified block diagram depictions of examples of a control/monitoring system 470 that can be utilized in conjunction with the microfluidic device 400. As shown, the system 470 can comprise a control module 472 and control/monitoring equipment 480. The control module 472 can be configured to control and monitor the device 400 directly and/or through the control/monitoring equipment 480.

The control module 472 can comprise a digital controller 474 and a digital memory 476. The controller 474 can be, for example, a digital processor, computer, or the like, and the digital memory 476 can be a non-transitory digital memory for storing data and machine executable instructions (e.g., software, firmware, microcode, or the like) as non-transitory data or signals. The controller 474 can be configured to operate in accordance with such machine executable instructions stored in the memory 476. Alternatively or in addition, the controller 474 can comprise hardwired digital circuitry and/or analog circuitry. The control module 472 can thus be configured to perform all or part of any process (e.g., process 100 of FIG. 1 and/or process 2500 of FIG. 25), step of such a process, function, act, or the like discussed herein.

The control/monitoring equipment 480 can comprise any of a number of different types of devices for controlling or monitoring the microfluidic device 400 and processes performed with the microfluidic device 400. For example, the equipment 480 can include power sources (not shown) for providing power to the microfluidic device 400; fluidic media sources (not shown but can comprise a flow controller like 226 of FIG. 2A) for providing fluidic media to or removing media from the microfluidic device 400; motive modules (not shown but can comprise a selector like 222 of FIG. 2A) for controlling selection and movement of micro-objects (not shown) in the microfluidic circuit 432; image capture mechanisms (not shown but can be like the detector 224 of FIG. 2A) for capturing images (e.g., of micro-objects) inside the microfluidic circuit 432; stimulation mechanisms (not shown) for directing energy into the microfluidic circuit 432 to stimulate reactions; or the like.

As noted, the control/monitoring equipment 480 can comprise motive modules for selecting and moving micro-objects (not shown) in the microfluidic circuit 432. A variety of motive mechanisms can be utilized. For example, dielectrophoresis (DEP) mechanisms (e.g., like the selector 222 of FIG. 2A) can be utilized to select and move micro-objects (not shown) in the microfluidic circuit. The base 404 and/or cover 422 of the microfluidic device 400 can comprise DEP configurations for selectively inducing DEP forces on micro-objects (not shown) in a fluidic medium (not shown) in the microfluidic circuit 432 to select, capture, and/or move individual micro-objects. The control/monitoring equipment 480 can include one or more control modules for such DEP configurations.

An example of such a DEP configuration of the support structure 404 or the cover 422 is an optoelectronic tweezers (OET) configuration. Examples of suitable OET configurations of the support structure 404 or cover 422 and associated monitoring and control equipment are illustrated in the following U.S. patent documents each of which is incorporated herein by reference in its entirety: U.S. Pat. No. 7,612,355; U.S. Pat. No. 7,956,339; U.S. Patent Application Publication No. 2012/0325665; U.S. Patent Application Publication No. 2014/0124370; U.S. patent application Ser. No. 14/262,140 (pending); and U.S. patent application Ser. No. 14/262,200 (pending). Micro-objects (not shown) can thus be individually selected, captured, and moved within the microfluidic circuit 432 of the microfluidic device 400 utilizing DEP devices and techniques such as OET.

As noted, the channel 434 and pens 436, 438, 440 can be configured to contain one or more fluidic media (not shown).

In the example shown in FIGS. 4A-4C, ports 424 are connected to the channel 434 and allow a fluidic medium (not shown) to be introduced into or removed from the microfluidic circuit 432. Once the microfluidic circuit 432 contains the fluidic medium (not shown), flows of fluidic media (not shown) can be selectively generated and stopped in the channel 434. For example, as shown, ports 424 can be disposed at different locations (e.g., opposite ends) of the channel 434, and a flow of medium (not shown) can be created from one port 424 functioning as an inlet to another port 424 functioning as an outlet.

As discussed above, each sequestration pen 436, 438, 440 can comprise a connection region 442 and an isolation region 444. The connection region 442 can comprise a proximal opening 452 to the channel 434 and a distal opening 454 to the isolation region 444. The channel 434 and each sequestration pen 436, 438, 440 can be configured so that the maximum penetration depth of a flow of medium (not shown) flowing in the channel 434 extends into the connection region 442 but not the isolation region 444.

Figure 5:
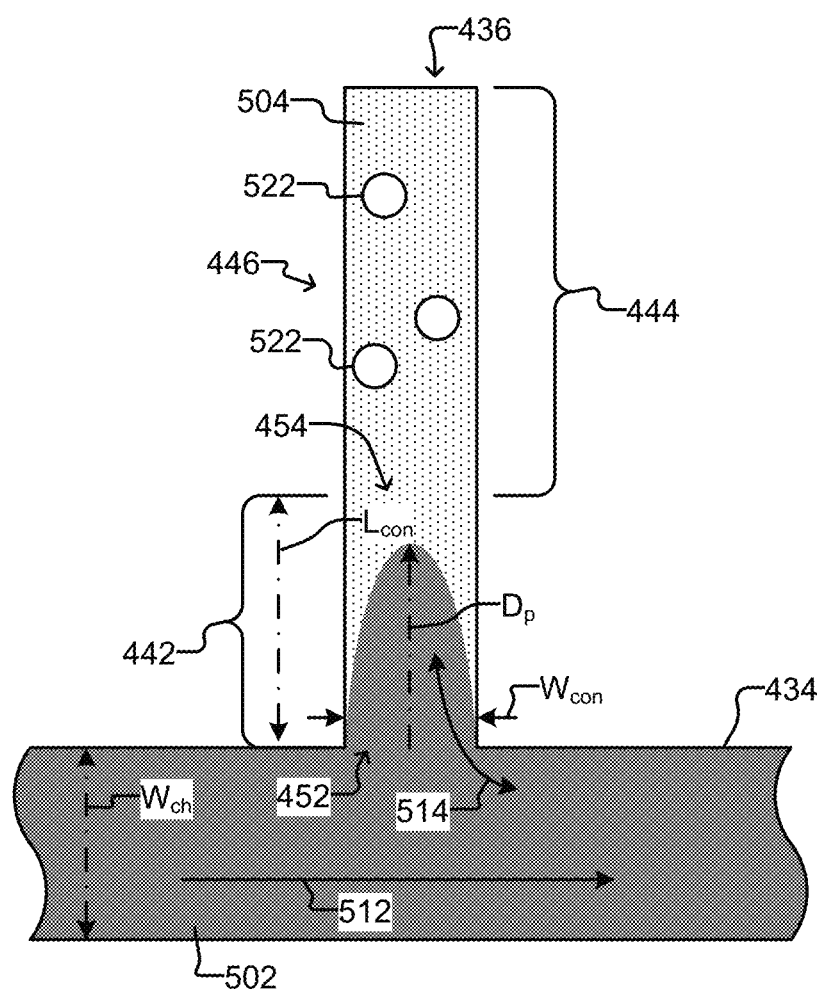
FIG. 5 illustrates an example of a sequestration pen in which a length of a connection region from a channel to an isolation region is greater than a penetration depth of medium flowing in the channel according to some embodiments of the invention.

FIG. 5 illustrates a detailed view of an example of a sequestration pen 436. Pens 438, 440 can be configured similarly. Examples of micro-objects 522 in pen 436 are also shown. As is known, a flow 512 of fluidic medium 502 in a microfluidic channel 434 past a proximal opening 452 of a pen 436 can cause a secondary flow 514 of the medium 502 into and/or out of the pen. To isolate micro-objects 522 in the isolation region 444 of a pen 436 from the secondary flow 514, the length $L_{con}$ of the connection region 442 of the sequestration pen 436 from the proximal opening 452 to the distal opening 454 can be greater than a maximum penetration depth $D_p$ of the secondary flow 514 into the connection region 442 when the velocity of the flow 512 in the channel 434 is at a maximum ($V_{max}$). As long as the flow 512 in the channel 434 does not exceed the maximum velocity $V_{max}$, the flow 512 and resulting secondary flow 514 can thus be limited to the channel 434 and the connection region 442 and kept out of the isolation region 444. The flow 512 in the channel 434 will thus not draw micro-objects 522 out of the isolation region 444. Micro-objects 522 in the isolation region 444 will thus stay in the isolation region 444 regardless of the flow 512 in the channel 432.

Moreover, the flow 512 will not move miscellaneous particles (e.g., microparticles and/or nanoparticles) from the channel 434 into the isolation region 444 of a pen 436, nor will the flow 512 draw miscellaneous particles from the isolation region 444 into the channel 434. Having the length $L_{con}$ of the connection region 442 be greater than the maximum penetration depth $D_p$ can thus prevent contamination of one pen 436 with miscellaneous particles from the channel 434 or another pen 438, 440.

Because the channel 434 and the connection regions 442 of the pens 436, 438, 440 can be affected by the flow 512 of medium 502 in the channel 434, the channel 434 and connection regions 442 can be deemed swept (or flow) regions of the microfluidic circuit 432. The isolation regions 444 of the pens 436, 438, 440, on the other hand, can be deemed unswept (or non-flow) regions. For example, a first medium 502 (e.g., components (not shown) in the first medium 502) in the channel 434 can mix with a second medium 504 (e.g., components (not shown) in the second medium 504) in the isolation region 444 substantially only by diffusion of the first medium 504 from the channel 434 through the connection region 442 and into the second medium 504 in the isolation region 444. Similarly, the second medium 504 (e.g., components (not shown) in the second medium 504) in the isolation region 444 can mix with the first medium 504 (e.g., components (not shown) in the first medium 502) in the channel 434 substantially only by diffusion of the second medium 502 from the isolation region 444 through the connection region 442 and into the first medium 502 in the channel 434. The first medium 502 can be the same medium or a different medium than the second medium 504. Moreover, the first medium 502 and the second medium 504 can start out being the same, then become different (e.g., through conditioning of the second medium by one or more biological micro-objects in the isolation region 444, or by changing the medium flowing through the channel 434).

The maximum penetration depth $D_p$ of the secondary flow 514 caused by the flow 512 in the channel 434 can depend on a number of parameters. Examples of such parameters include: the shape of the channel 434 (e.g., the channel can direct medium into the connection region 442, divert medium away from the connection region 442, or simply flow past the connection region 442); a width $W_{ch}$ (or cross-sectional area) of the channel 434 at the proximal opening 452; a width $W_{con}$ (or cross-sectional area) of the connection region 442 at the proximal opening 452; the maximum velocity $V_{max}$ of the flow 512 in the channel 434; the viscosity of the first medium 502 and/or the second medium 504, or the like.

In some embodiments, the dimensions of the channel 434 and sequestration pens 436, 438, 440 can be oriented as follows with respect to the flow 512 in the channel 434: the channel width $W_{ch}$ (or cross-sectional area of the channel 434) can be substantially perpendicular to the flow 512, the width $W_{con}$ (or cross-sectional area) of the connection region 442 at the proximal opening 552 can be substantially parallel to the flow 512, and the length $L_{con}$ of the connection region can be substantially perpendicular to the flow 512. The foregoing are examples only, and the dimensions of the channel 434 and sequestration pens 436, 438, 440 can be in other orientations with respect to each other.

In some embodiments, the width $W_{ch}$ of the channel 434 at a proximal opening 452 can be within any of the following ranges: 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width $W_{ch}$ of the channel 434 can be in other ranges (e.g., a range defined by any of the endpoints listed above).

In some embodiments, the height $H_{ch}$ of the channel 134 at a proximal opening 152 can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the channel 434 can be in other ranges (e.g., a range defined by any of the endpoints listed above).

In some embodiments, a cross-sectional area of the channel 434 at a proximal opening 452 can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the channel 434 at a proximal opening 452 can be in other ranges (e.g., a range defined by any of the endpoints listed above).

In some embodiments, the length of the connection region $L_{con}$ can be in any of the following ranges: 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length $L_{con}$ of a connection region 442 can be in a different ranges than the foregoing examples (e.g., a range defined by any of the endpoints listed above).

In some embodiments, the width $W_{con}$ of a connection region 442 at a proximal opening 452 can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region 442 at a proximal opening 452 can be different than the foregoing examples (e.g., a range defined by any of the endpoints listed above).

In other embodiments, the width $W_{con}$ of a connection region 442 at a proximal opening 452 can be in any of the following ranges: 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only, and the width $W_{con}$ of a connection region 442 at a proximal opening 452 can be different than the foregoing examples (e.g., a range defined by any of the endpoints listed above).

In some embodiments, a ratio of the length $L_{con}$ of a connection region 442 to a width $W_{con}$ of the connection region 442 at the proximal opening 452 of can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 442 to a width $W_{con}$ of the connection region 442 at the proximal opening 452 can be different than the foregoing examples.

Figure 6:
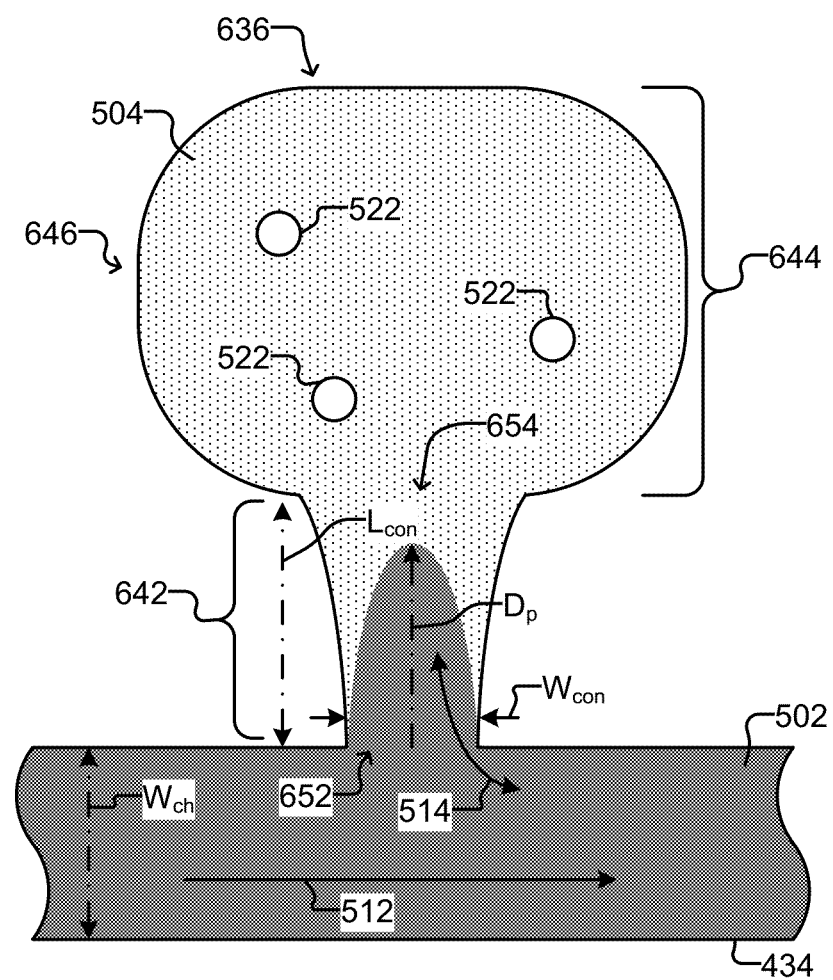
FIG. 6 is another example of a sequestration pen comprising a connection region from a channel to an isolation region that is longer than a penetration depth of medium flowing in the channel according to some embodiments of the invention.
Figure 7A:
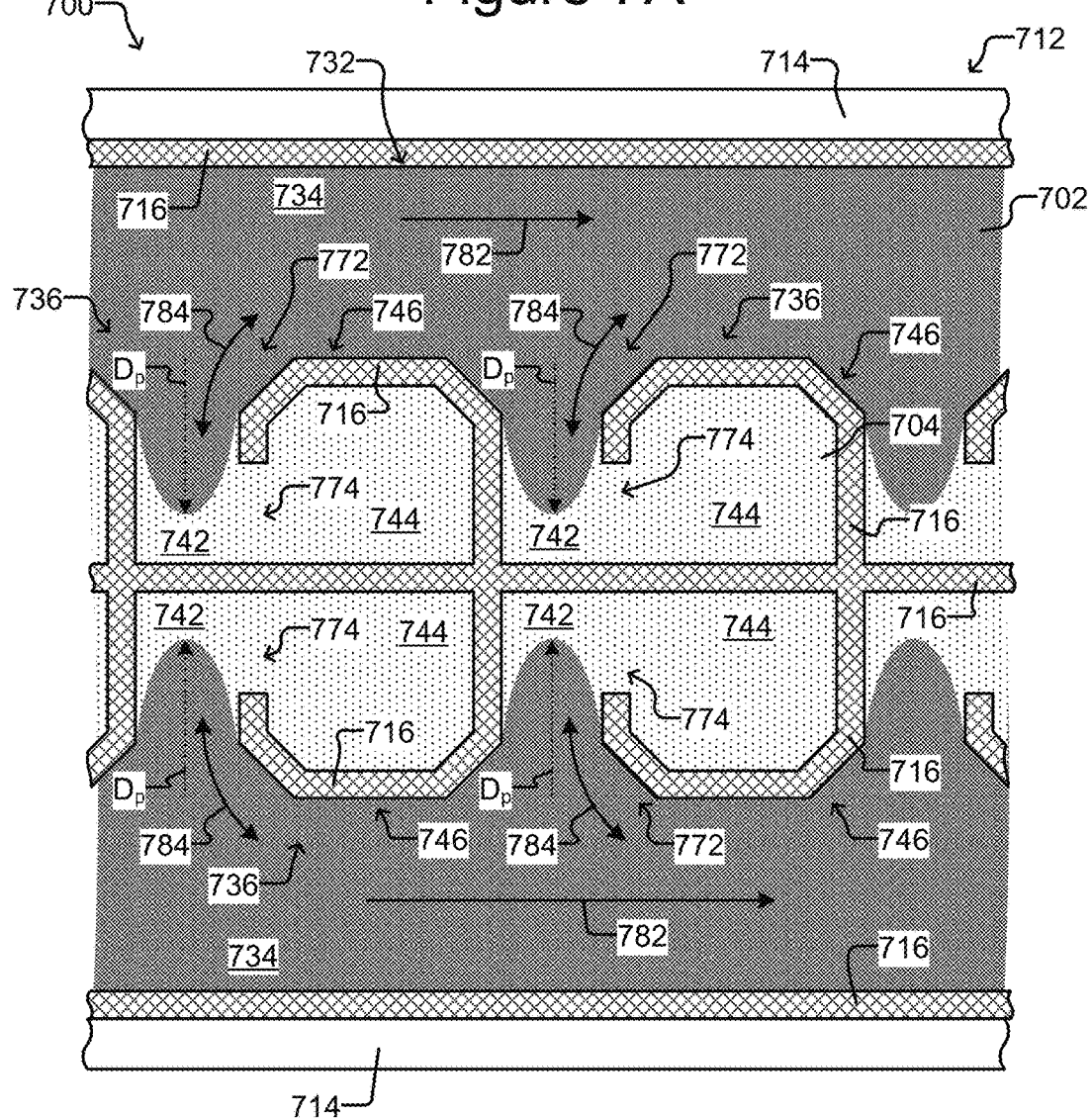
Figures 7B, 7C:
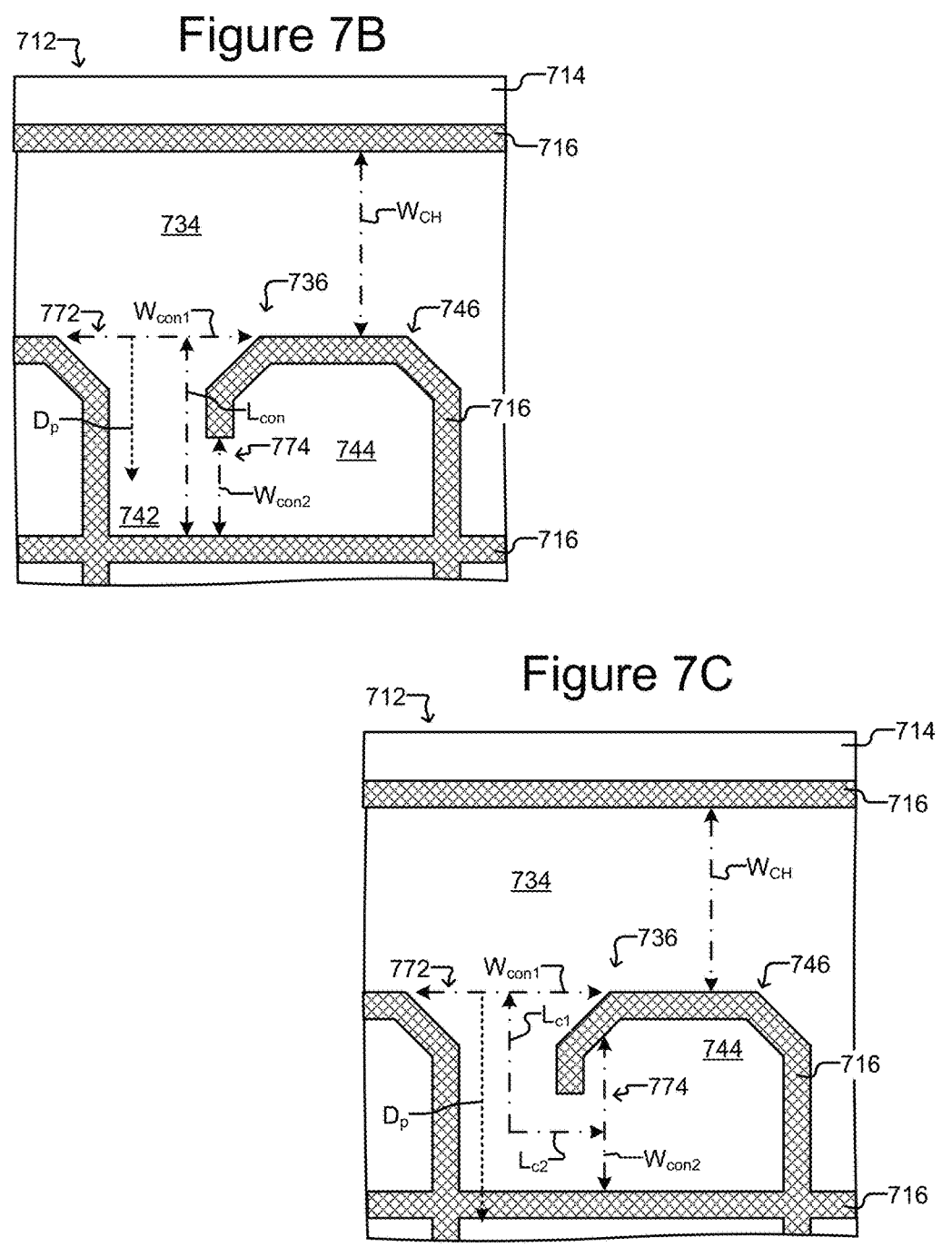

As illustrated in FIG. 5, the width $W_{con}$ of the connection region 442 can be uniform from the proximal opening 452 to the distal opening 454. The width $W_{con}$ of the connection region 442 at the distal opening 454 can thus be in any of the ranges identified above for the width $W_{con}$ of the connection region 442 at the proximal opening 452. Alternatively, the width $W_{con}$ of the connection region 442 at the distal opening 454 can be larger (e.g., as shown in FIG. 6) or ma (e.g., as shown in FIGS. 7A-7C) than the width $W_{con}$ of the connection region 442 at the proximal opening 452.

As also illustrated in FIG. 5, the width of the isolation region 444 at the distal opening 454 can be substantially the same as the width $W_{con}$ of the connection region 442 at the proximal opening 452. The width of the isolation region 444 at the distal opening 454 can thus be in any of the ranges identified above for the width $W_{con}$ of the connection region 442 at the proximal opening 452. Alternatively, the width of the isolation region 444 at the distal opening 454 can be larger (e.g., as shown in FIG. 6) or smaller (not shown) than the width $W_{con}$ of the connection region 442 at the proximal opening 452.

In some embodiments, the maximum velocity $V_{max}$ of a flow 512 in the channel 434 is the maximum velocity that the channel can maintain without causing a structural failure in the microfluidic device in which the channel is located. The maximum velocity that a channel can maintain depends on various factors, including the structural integrity of the microfluidic device and the cross-sectional area of the channel. For exemplary microfluidic devices of the present invention, the maximum flow velocity $V_{max}$ in a channel having a cross-sectional area of around 3,000 to 4,000 square microns is around 10 µL/sec. Alternatively, the maximum velocity $V_{max}$ of a flow 512 in channel 434 can be set so as to ensure that isolation regions 444 are isolated from the flow 512 in channel 434. In particular, based on the width $W_{con}$ of the proximal opening 452 of a connection region 442 of a sequestration pen 436, 438, 440, $V_{max}$ can be set so as to ensure that the depth of penetration $D_p$ of a secondary flow 514 into the connection region is less than $L_{on}$. For example, for a sequestration pen having a connection region with a proximal opening 452 having a width $W_{con}$ of about 30 to 40 microns, $V_{max}$ can be set around 0.2, 0.3, 0.4, 0.5, 0.6, 0.7, 0.8, 0.9, 1.0, 1.1, 1.2, 1.3, 1.4, or 1.5 µL/sec.

In some embodiments, the sum of the length $L_{con}$ of the connection region 442 and a corresponding length of the isolation region 444 of a sequestration pen 436, 438, 440 can be sufficiently short for relatively rapid diffusion of components of a second medium 504 in the isolation region 444 to a first medium 502 in the channel 434. For example, in some embodiments, the sum of (1) the length $L_{con}$ of the connection region 442 and (2) the distance between a biological micro-object located in isolation region 444 of a sequestration pen 436, 438, 440 and the distal opening 454 of the connection region can be in the following ranges: 40 microns to 300 microns, 50 microns to 550 microns, 60 microns to 500 microns, 70 microns to 180 microns, 80 microns to 160 microns, 90 microns to 140 microns, 100 microns to 120 microns, or any range including one of the foregoing end points. The rate of diffusion of a molecule (e.g., an analyte of interest, such as an antibody) is dependent on a number of factors, including temperature, viscosity of the medium, and the coefficient of diffusion $D_0$ of the molecule. The $D_0$ for an IgG antibody in aqueous solution at 20° C. is around $4.4 \times 10^{-7}$ cm$^2$/sec, while the viscosity of biological micro-object culture medium is around 9×10-4 m2/sec. Thus, for example, an antibody in biological micro-object culture medium at 20° C. can have a rate of diffusion of around 0.5 microns/sec. Accordingly, in some embodiments, a time period for diffusion from a biological micro-object located in isolation region 444 into the channel 434 can be about 10 minutes or less (e.g., 9, 8, 7, 6, 5 minutes, or less). The time period for diffusion can be manipulated by changing parameters that influence the rate of diffusion. For example, the temperature of the media can be increased (e.g., to a physiological temperature such as 37° C.) or decreased (e.g., to 15° C., 10° C., or 4° C.) thereby increasing or decreasing the rate of diffusion, respectively.

The configuration of sequestration pen 436 illustrated in FIG. 5 is but an example, and many variations are possible. For example, the isolation region 444 is illustrated as sized to contain a plurality of micro-objects 522, but the isolation region 444 can be sized to contain only one, two, three, four, five, or similar relatively small numbers of micro-objects 522. Accordingly, the volume of an isolation region 444 can be, for example, at least $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$ cubic microns, or more.

As another example, the sequestration pen 436 is shown extending generally perpendicularly from the channel 434 and thus forming generally 90° angles with the channel 434. The sequestration pen 436 can alternatively extend from the channel 434 at other angles such as, for example, any angle between 30° and 150°.

As yet another example, the connection region 442 and the isolation region 444 are illustrated in FIG. 5 as substantially rectangular, but one or both of the connection region 442 and the isolation region 444 can be other shapes. Examples of such shapes include oval, triangular, circular, hourglass-shaped, and the like.

As still another example, the connection region 442 and the isolation region 444 are illustrated in FIG. 5 as having substantially uniform widths. That is, in FIG. 5, the width $W_{con}$ of the connection region 442 is shown as being uniform from the proximal opening 452 to the distal opening 454; a corresponding width of the isolation region 444 is similarly uniform; and the width $W_{con}$ of the connection region 442 and a corresponding width of the isolation region 444 are shown as equal. Any of the foregoing can be different than shown in FIG. 5. For example, a width $W_{con}$ of the connection region 442 can vary from the proximal opening 452 to the distal opening 454 (e.g., in the manner of a trapezoid or an hourglass); a width of the isolation region 444 can vary (e.g., in the manner of a triangle or flask); and a width $W_{con}$ of the connection region 442 can be different than a corresponding width of the isolation region 444.

FIG. 6 illustrates an example of a sequestration pen illustrating examples of some of the foregoing variations. The pen shown in FIG. 6 can replace any of pens 436, 438, 440 in any of the figures or discussions herein.

The sequestration pen of FIG. 6 can comprise a connection region 642 and an isolation structure 646 comprising an isolation region 644. The connection region 642 can comprise a proximal opening 652 to the channel 434 and a distal opening 654 to the isolation region 644. In the example illustrated in FIG. 6, the connection region 642 expands such that its width $W_{con}$ increases from the proximal opening 652 to the distal opening 654. Other than shape, however, the connection region 642, isolation structure 646, and isolation region 644 can be generally the same as the connection region 442, isolation structure 446, and isolation region 444 of FIG. 5 as discussed above.

For example, the channel 434 and the sequestration pen of FIG. 6 can be configured so that the maximum penetration depth $D_p$ of the secondary flow 514 extends into the connection region 642 but not into the isolation region 644. The length $L_{con}$ of the connection region 642 can thus be greater than the maximum penetration depth $D_p$, generally as discussed above with respect to FIG. 5. Also as discussed above, micro-objects 522 in the isolation region 644 will thus stay in the isolation region 644 as long as the velocity of the flow 512 in the channel 434 does not exceed the maximum flow velocity $V_{max}$. The channel 434 and connection region 642 are thus examples of swept (or flow) regions, and the isolation region 644 is an example of an unswept (or non-flow) region.

FIGS. 7A-7C show examples of variations of the microfluidic circuit 432 and channel 434 of FIGS. 4A-4C, as well as additional examples of variations of sequestration pens 436, 438, 440. The sequestration pens 736 shown in FIGS. 7A-7C can replace any of the pens 436, 438, 440 in any of the figures or discussions herein. Likewise, the microfluidic device 700 can replace the microfluidic device 400 in any of the figures or discussions herein.

The microfluidic device 700 of FIGS. 7A-7C can comprise a support structure (not visible but can be like 404 of FIG. 4A-4C), a microfluidic circuit structure 712, and a cover (not visible but can be like 422). The microfluidic circuit structure 712 can comprise a frame 714 and microfluidic circuit material 716, which can be the same as or generally similar to the frame 414 and microfluidic circuit material 416 of FIGS. 4A-4C. As shown in FIG. 7A, the microfluidic circuit 732 defined by the microfluidic circuit material 716 can comprise multiple channels 734 (two are shown but there can be more) to which multiple sequestration pens 736 are fluidically connected.

Each sequestration pen 736 can comprise an isolation structure 746, an isolation region 744 within the isolation structure 746, and a connection region 742. From a proximal opening 772 at the channel 734 to a distal opening 774 at the isolation structure 736, the connection region 742 can fluidically connect the channel 734 to the isolation region 744. Generally in accordance with the discussion above of FIG. 5, a flow 782 of a first fluidic medium 702 in a channel 734 can create secondary flows 784 of the first medium 702 from the channel 734 into and/or out of the connection regions 742 of pens 736 that are connected to the channel 734.

As illustrated in FIG. 7B, the connection region 742 can include the area between the proximal opening 772 to a channel 734 and the distal opening 774 to an isolation structure 746. The length $L_{con}$ of the connection region 742 can be greater than the maximum penetration depth $D_p$ of secondary flow 784, in which case the secondary flow 784 will extend into the connection region 742 without being redirected toward the isolation region 744 (as shown in FIG. 7A). Alternatively, as illustrated in FIG. 7C, the connection region 742 can have a length $L_{con}$ that is less than the maximum penetration depth $D_p$, in which case the secondary flow 784 will extend through the connection region 742 and can be redirected toward the isolation region 744. In this latter situation, the sum of lengths $L_{c1}$ and $L_{c2}$ of connection region 742 can be greater than the maximum penetration depth $D_p$. In this manner, secondary flow 784 will not extend into isolation region 744. Whether length $L_{con}$ of connection region 742 is greater than the penetration depth $D_p$ or the sum of lengths $L_{c1}$ and $L_{c2}$ of connection region 742 is greater than the penetration depth $D_p$, a flow 782 of a first medium 702 in channel 734 that does not exceed a maximum velocity $V_{max}$ will produce a secondary flow having a penetration depth $D_p$, and micro-objects (not shown but can be like 522 in FIG. 5) in the isolation region 744 of a pen 736 will not be drawn out of the isolation region 744 by a flow 782 of first medium 702 in a channel 734. Nor will the flow 782 in the channel 734 draw miscellaneous materials (not shown) from a channel 734 into the isolation region 744 of a pen 736 or from the isolation region 744 into the channel 734. Diffusion is the only mechanism by which components in a first medium 702 in the channel 734 can move from the channel 734 into a second medium 704 in an isolation region 744 of a pen 736. Likewise, diffusion is the only mechanism by which components in a second medium 704 in an isolation region 744 of a pen 736 can move from the isolation region 744 to a first medium 702 in the channel 734. The first medium 702 can be the same medium as the second medium 704, or the first medium 702 can be a different medium than the second medium 704. Alternatively, the first medium 702 and the second medium 704 can start out being the same, then become different (e.g., through conditioning of the second medium by one or more biological micro-objects in the isolation region 744, or by changing the medium flowing through the channel 734).

As illustrated in FIG. 7B, the width $W_{ch}$ of a channel 734 perpendicular to the direction of a flow 782 (see FIG. 7A) in the channel 734 can be substantially perpendicular to a width $W_{con1}$ of the proximal opening 772 and thus substantially parallel to a width $W_{con2}$ of the distal opening 774. The width $W_{con1}$ of the proximal opening 772 and the width $W_{con2}$ of the distal opening 774, however, need not be substantially perpendicular to each other. For example, an angle between an axis (not shown) on which the width $W_{con1}$ of the proximal opening 772 is oriented and another axis on which the width $W_{con2}$ of the distal opening 774 is oriented can be other than perpendicular and thus other than 90°. Examples of alternatively angles include angles in any of the following ranges: between 30° and 90°, between 45° and 90°, between 60° and 90°, or the like.

With regard to the foregoing discussion about microfluidic devices having a channel and one or more sequestration pens, a fluidic medium (e.g., a first medium and/or a second medium) can be any fluid that is capable of maintaining a biological micro-object in a substantially assayable state. The assayable state will depend on the biological micro-object and the assay being performed. For example, if the biological micro-object is a biological micro-object that is being assayed for the secretion of a protein of interest, the biological micro-object would be substantially assayable provided that it is viable and capable of expressing and secreting proteins.

FIGS. 8-30 illustrate examples of the process 100 of FIG. 1 testing biological micro-objects (e.g., biological cells) in the microfluidic device 200 of FIGS. 2A-2C or the microfluidic device 400 of FIGS. 4A-4C. The process 100 is not, however, limited to sorting biological micro-objects or operating on the microfluidic devices 200, 400. Nor are the microfluidic devices 200, 400 limited to performing the process 100. Moreover, while aspects of the steps of process 100 may be discussed in connection with device 200 but not device 400, or vice versa, such aspects can be applied in the other device or any other similar micro-fluidic devices.

Figure 8:
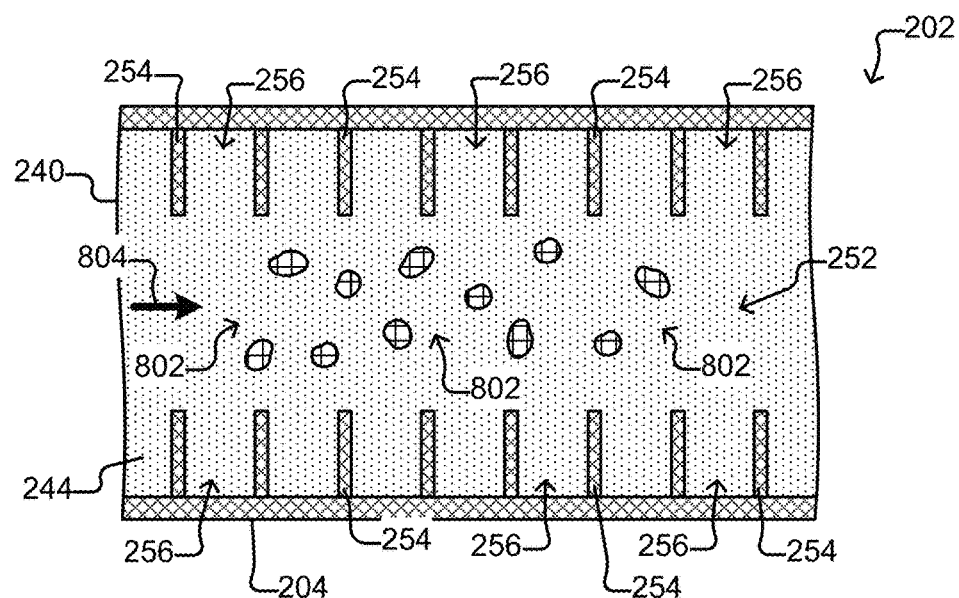
FIG. 8 shows an example of loading biological micro-objects into a flow path of the microfluidic device of FIGS. 2A-2C according to some embodiments of the invention.
Figure 9:
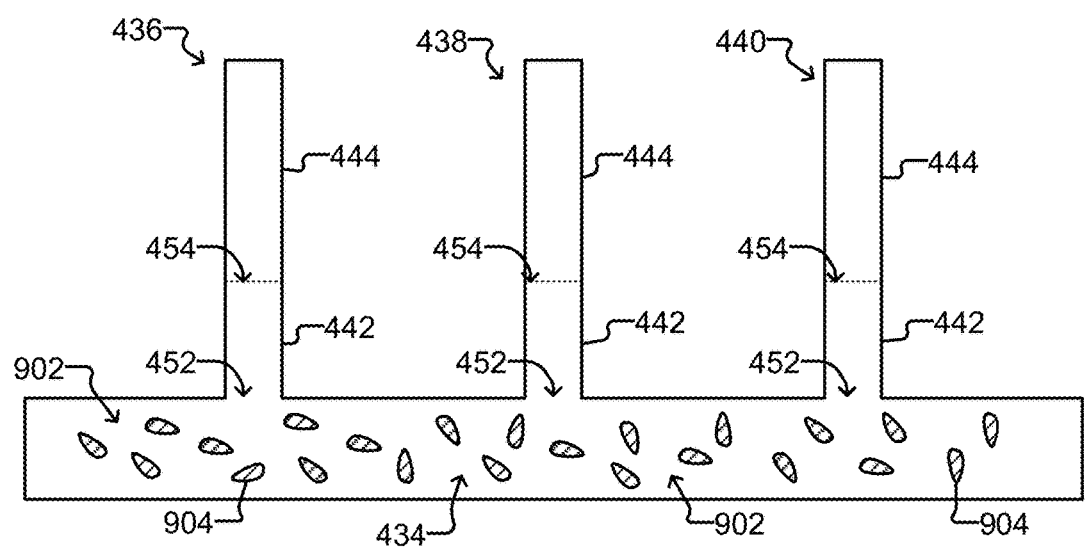
FIG. 9 illustrates an example of flowing biological micro-objects into a channel of the microfluidic device of FIGS. 4A-4C according to some embodiments of the invention.

At step 102, the process 100 can load biological micro-objects into a micro-fluidic device. FIG. 8 illustrates an example in which biological micro-objects 802 (e.g., biological cells) are loaded into a flow region 240 (e.g., the channel 252) of the microfluidic device 200. FIG. 9 shows an example in which sample material 902 comprising biological micro-objects 904 is flowed into a channel 434 of the microfluidic device 400.

As shown in FIG. 8 (which like FIGS. 10, 11, 13, 14, 17, 18, 26, and 27, illustrates a partial, top, cross-section view into the flow region 240 of the device 200), a mixture of biological micro-objects 802 can be loaded into the channel 252 of the microfluidic device 200. For example, the biological micro-objects 802 can be input into the device 200 through the inlet 208 (see FIGS. 2A-2C), and the biological micro-objects 802 can move with a flow 804 of medium 244 in the channel 252. The flow 804 can be a convection flow.

Once the biological micro-objects 802 are in the channel 252 and adjacent to the pens 256, the flow 804 can be stopped or slowed to keep the biological micro-objects 802 in the flow channel 252 adjacent to the pens 256 for a time sufficient to perform steps 104 and 106. The mixture of biological micro-objects 802 loaded in the channel 252 can comprise different types of biological micro-objects and other components such as debris, proteins, contamination, particles, and the like.

FIG. 9 illustrates an example in which sample material 902 comprising biological micro-objects 904 is flowed into a channel 434 of the microfluidic device 400. In addition to the biological micro-objects 904, the sample material 902 can comprise other micro-objects (not shown) or materials (not shown). In some embodiments, the channel 434 can have a cross-sectional area disclosed herein, e.g., about 3,000 to 6,000 square microns or about 2,500 to 4,000 square microns. The sample material 902 can be flowed into the channel 434 at a rate disclosed herein, e.g., about 0.05 to 0.25 µL/sec (e.g., about 0.1 to 0.2 µL/sec or about 0.14 to 0.15 µL/sec). In some embodiments, the control module 472 of FIG. 4A can cause the control/monitoring equipment 480 to flow a first fluidic medium (not shown) containing the sample material 902 through a port 424 into the channel 434. Once the sample material 902 is in the channel 434, flow of the medium (not shown) in the channel 434 can be slowed or substantially stopped. Starting and stopping flow of medium (not shown) in the channel 434 can include opening and closing values (not shown) that comprise the passages 426 of the ports 424.

The biological micro-objects 802, 904 can be any biological micro-object 802, 904 to be assayed for production of a particular analyte or analytes of interest. Examples of biological micro-objects 802, 904 include biological micro-objects such as mammalian biological micro-objects, human biological micro-objects, immunological biological micro-objects (e.g., T biological micro-objects, B biological micro-objects, macrophages, etc.), B biological micro-object hybridomas, stem biological micro-objects (e.g., bone marrow-derived stem biological micro-objects, adipose-derived stem biological micro-objects, etc.), transformed biological micro-objects lines (e.g., transformed CHO biological micro-objects, HeLa biological micro-objects, HEK biological micro-objects, etc.), insect biological micro-objects (e.g., Sf9, Sf21, HighFive, etc.), protozoan biological micro-objects (e.g., *Leishmania tarentolae*), yeast biological micro-objects (e.g., *S. saccharomyces, P. pastoris*, etc.), bacterial biological micro-objects (e.g., *E. coli, B. subtilis, B. thuringiensis*, etc.), any combination of the foregoing, or the like. Examples of biological micro-objects 904 also include embryos, such as mammalian embryos (e.g., human, primate, ursidae, canine, feline, bovine, ovis, capra, equus, porcine, etc.), or the like. Examples of the analyte of interest include a protein, a carbohydrate, a lipid, a nucleic acid, a metabolite, or the like. Other examples of the analyte of interest include a material that comprises an antibody such as an IgG (e.g., an IgG1, IgG2, IgG3, or IgG4 sub-class), an IgM, IgA, IgD, or IgE class antibody.

Figure 10:
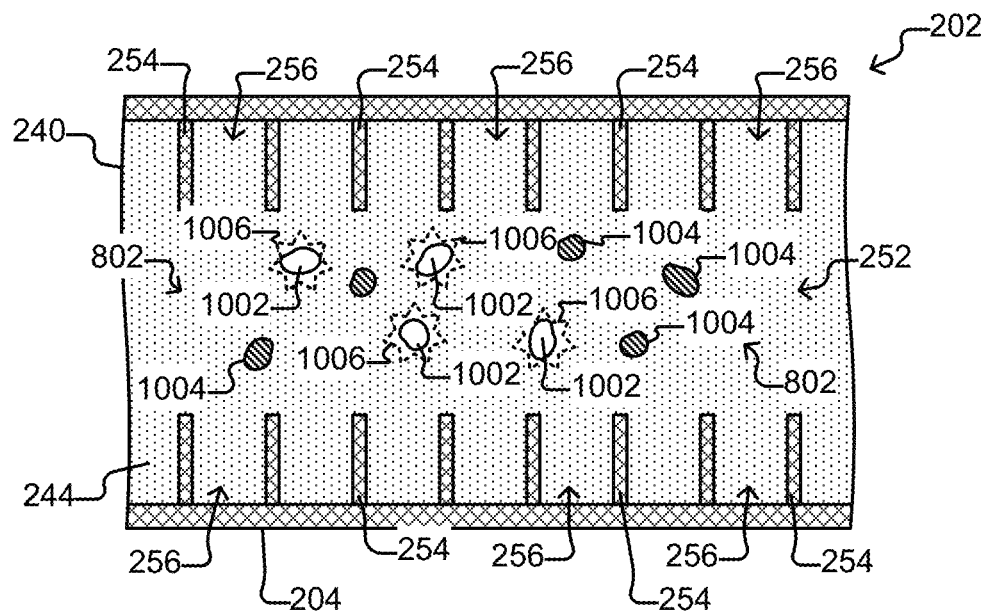
FIG. 10 illustrates an example of testing the biological micro-objects in the flow path of the microfluidic device of FIGS. 2A-2C for a first characteristic according to some embodiments of the invention.
Figure 11:
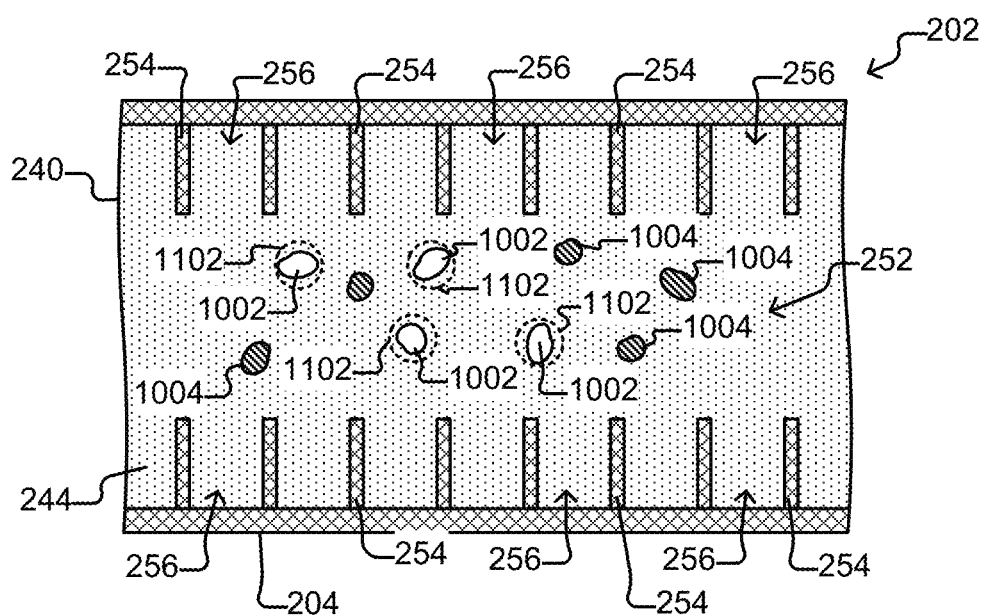
FIG. 11 is an example of selecting biological micro-objects in the microfluidic device of FIGS. 2A-2C according to some embodiments of the invention.
Figure 12:
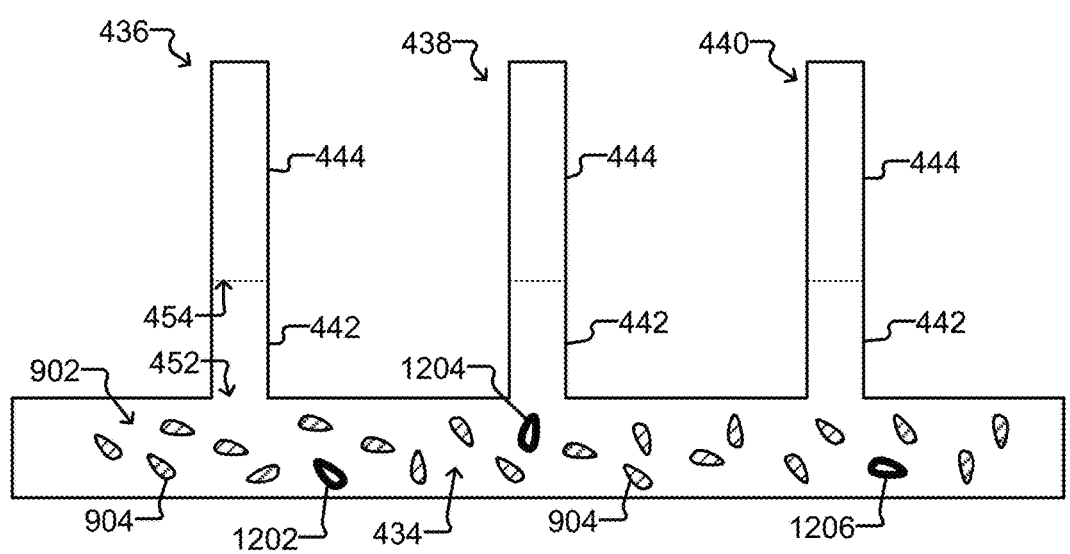
FIG. 12 illustrates an example of selecting biological micro-objects in the microfluidic device of FIGS. 4A-4C according to some embodiments of the invention.

At step 104, the process 100 can perform a first test on the biological micro-objects loaded into the micro-fluidic device at step 102. Step 104 can include selecting ones of the biological micro-objects in accordance with the first test. Alternatively, step 104 can include selecting one of the biological micro-objects without performing the first test. FIG. 10 illustrates an example of a first test performed on the biological micro-objects 802 in the channel 252 of the microfluidic device 200, and FIG. 11 illustrates an example of selecting the biological micro-objects 802 in accordance with the first test. (The selected biological micro-objects are labeled 1002 in FIG. 11 and thereafter.) FIG. 12 shows an example in which biological micro-objects 1202, 1204, 1206 are selected from among the micro-objects 904 in the channel 434 of the microfluidic device 400.

The first test can comprise any number of possible tests. For example, the first test, whether performed in the microfluidic device 200 or 400, can test for a first characteristic of the biological micro-objects 802 or biological micro-objects 904. The first test performed at step 104 can be any test that tests for any desired characteristic. For example, the desired characteristic can relate to the size, shape, and/or morphology of the biological micro-objects 802 or biological micro-objects 904. The first test can comprise capturing images of the biological micro-objects 802 or biological micro-objects 904 and analyzing the images to determine which of the biological micro-objects 802 or biological micro-objects 904 have the desired characteristic. As another example, the first test performed at step 104 can determine which of the biological micro-objects 802 or biological micro-objects 904 exhibit a particular detectable condition that indicates the first characteristic. For example, the first characteristic could be expression of one or more cell-surface markers and the first test performed at step 104 could detect the presence or absence of such cell-surface markers on the biological micro-objects 802, 904. By testing for an appropriate cell-surface marker or combination of cell-surface markers, particular cell types can be identified and selected at step 104. Examples of such particular cell types can include healthy cells, cancer cells, infected cells (e.g., infected with a virus or a parasite), immunological cells (e.g., B cells, T cells, macrophages), stem cells, and the like.

In the example shown in FIG. 10, the detectable condition of the biological micro-objects 802 in microfluidic device 200 is radiation of energy 1006, which can be, for example, electromagnetic radiation. The biological micro-objects 802 can be pre-treated (prior to being loaded into the microfluidic device 200 or in the channel 252) with an assay material (not shown) that causes the biological micro-objects 802 that have the first characteristic to radiate energy 1006.

Examples of the first characteristic tested at step 104 can include, without limitation, a biological state (e.g., cell type) or a particular biological activity of the biological micro-objects 802. For example, the first characteristic can be an observable physical characteristic, such as size, shape, color, texture, surface morphology, identifiable sub-components, or other characteristic marks. Alternatively, the first characteristic can be an assayable characteristic, such as permeability, conductivity, capacitance, response to changes in the environment, or producing (e.g., expressing, secreting or the like) a particular biological material of interest. The particular biological material of interest can be a cell-surface marker (e.g., a membrane associated protein, glycoprotein, or the like). Another example of a particular biological material of interest is a therapeutic protein, such as an antibody (e.g., IgG-type antibody) that specifically binds to an antigen of interest. Thus, selected biological micro-objects 1002 can be one or more of the biological micro-objects 802 that test positive for producing (e.g., expressing) a particular biological material such as a cell-surface marker, and unselected biological micro-objects 1004 can be biological micro-objects 802 that do not test positive for the foregoing. Suitable assay materials with which the biological micro-objects 802 can be pretreated include a reagent that both binds to the particular biological material of interest and includes labels that radiate the energy 1006.

As shown in FIG. 11, biological micro-objects 1002 can be selected by trapping the micro-objects 1002 with a light trap 1102. The light traps 1102 can be generated, moved, and turned off in the channel 252 of the microfluidic device 200 by directing changing patterns of light into the channel 252 generally as discussed above with respect to FIGS. 3A and 3B. Unselected biological micro-objects are labeled 1004 in FIG. 11. In the example illustrated in FIG. 11, light traps 1102 are not generated for the unselected biological micro-objects 1004.

FIG. 12 illustrates selecting, at step 104, biological micro-objects 1202, 1204, 1206 from among the biological micro-objects 904 in the channel 434 of the microfluidic device 400. The selection can be in response to the results of a first test performed at step 104. Alternatively, the selection of micro-objects 1202, 1204, 1206 can be a random selection and thus made without performing the first test. If based on a first test, step 104 can, for example, comprise selecting the biological micro-objects 1202, 1204, 1206 for one or more observable physical characteristics or assayable characteristics, as discussed above. For example, biological micro-objects 1202, 1204, 1206 can be selected from the micro-objects 904 in the sample material 902 based on any of a number of possible detectable characteristics, such as biological micro-object-type specific characteristics and/or characteristics associate with biological micro-object viability or health. Examples of such characteristics include size, shape, color, texture, permeability, conductivity, capacitance, expression of biological micro-object-type specific markers, response to changes in the environment, or the like. In one particular embodiment, biological micro-objects 904 having a rounded shape in cross-section with a diameter in any of the following ranges can be selected from the sample material 602: 0.5-2.5 microns, 1-5 microns, 2.5-7.5 microns, 5-10 microns, 5-15 microns, 5-20 microns, 5-25 microns, 10-15 microns, 10-20 microns, 10-25 microns, 10-30 microns, 15-20 microns, 15-25 microns, 15-30 microns, 15-35 microns, 20-25 microns, 20-30 microns, 20-35 microns, or 20-40 microns. As another example, biological micro-objects 604 whose size is between 100 and 500 microns (e.g., between 100 and 200 microns, 150 and 300 microns, 200 to 400 microns, or 250 to 500 microns) can be selected from the sample material 902.

Although the example shown in FIG. 12 illustrates selecting micro-objects 1202, 1204, 1206 in the channel 434, the sample material 902 can alternatively be at least partially in the connection region 442 of a pen 436, 438, 440. The micro-objects 1202, 1204, 1206 can thus be selected while in the connection regions 442.

In some embodiments, the control module 472 can perform the first test at step 104 by causing the control/monitoring equipment 480 to capture images of the biological micro-objects 904 in the sample material 902. The control module 472, which can be configured with known image analysis algorithms, can analyze the images and identify ones of the biological micro-objects 904 that have the desired characteristics. Alternatively, a human user can analyze the captured images.

For assaying characteristics of biological micro-objects, a human user and/or the control module 472 can control the assaying. For example, biological micro-objects such as biological micro-objects can be assayed for permeability, conductivity, or biological micro-object-type specific markers (e.g., using antibodies specific to biological micro-object-surface proteins).

Figure 15:
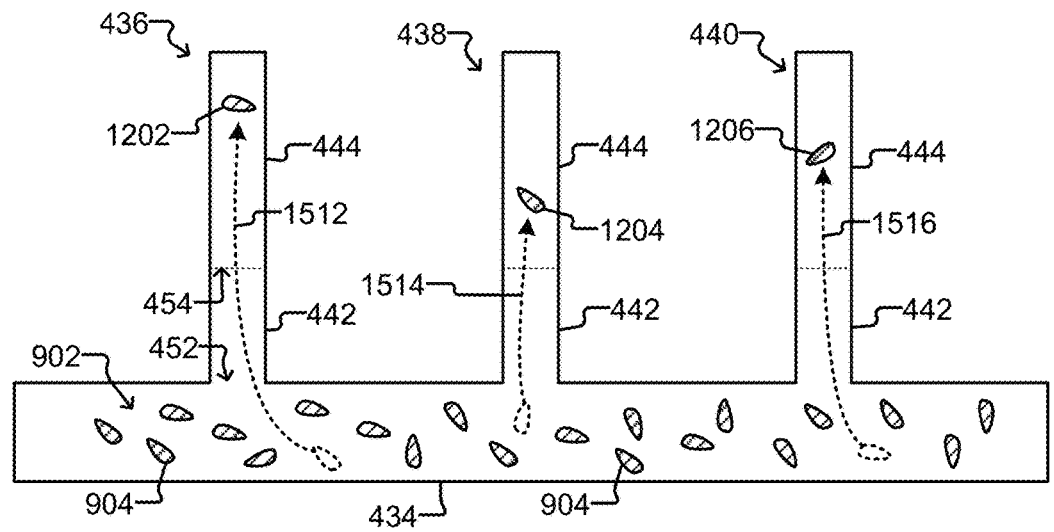
FIG. 15 shows an example of moving selected biological micro-objects from the channel into sequestration pens of the microfluidic device of FIGS. 4A-4C according to some embodiments of the invention.
Figure 16:
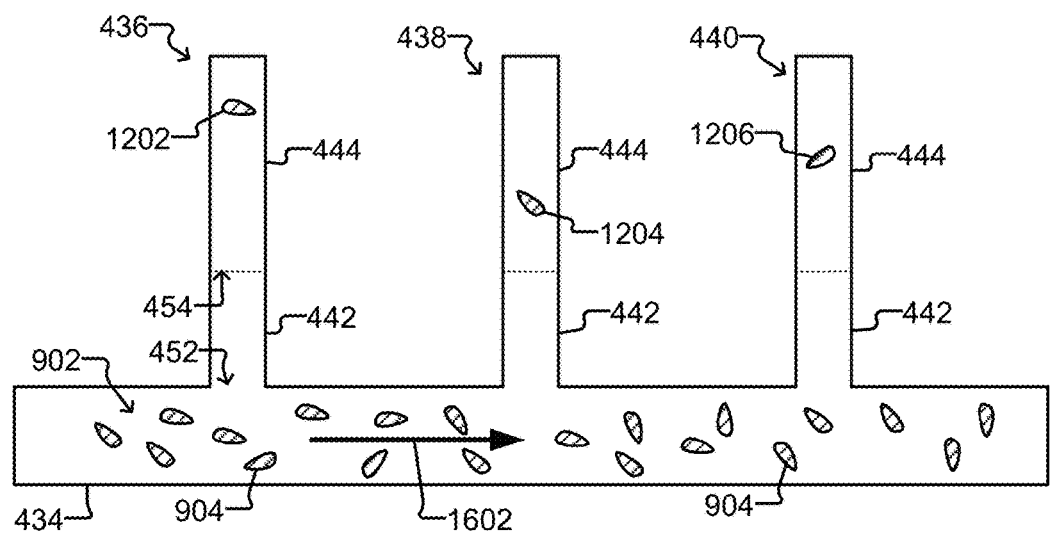
FIG. 16 is an example of flushing biological micro-objects from a channel in the microfluidic device of FIGS. 4A-4C according to some embodiments of the invention.

At step 106, the process 100 can separate the selected biological micro-objects or biological micro-objects selected as part of step 104. However, if biological micro-objects are selected without performing a first step at step 104, step 106 can be skipped or can consist of simply flushing unselected biological micro-objects out of channel 252 (and, optionally, out of flow region 240 as well). FIGS. 13 and 14 illustrate an example in which selected biological micro-objects 1002 are moved to the holding pens 256 in the microfluidic device 200, and unselected biological micro-objects 1004 are flushed out of the channel 252. FIGS. 15 and 16 show an example in which selected biological micro-objects 1202, 1204, 1206 are moved into the isolation regions 444 of pens 436, 438, 440 of the microfluidic device 400, after which the unselected micro-objects 904 are flushed out of the flow channel 434.

As noted above with respect to FIG. 11, each biological micro-object 1002 can be selected with a light trap 1102. For example, the selector 222 (see FIGS. 2A-2C) configured as the DEP device 300 of FIGS. 3A and 3B can generate light traps 1102 that trap individual selected biological micro-objects 1002. As shown in FIG. 13, the DEP device 300 can then move the light traps 1102 into the pens 256, which moves the trapped selected biological micro-objects 1002 into the pens 256. As illustrated, each selected biological micro-object 1002 can be individually trapped and moved into a holding pen 256. Alternatively, more than one selected biological micro-object 1002 can be trapped by a single trap 1102, and/or more than one selected biological micro-object 1002 can be moved into any one pen 256. Regardless, two or more of the selected biological micro-objects 1002 can be selected in the channel 252 and moved in parallel into the pens 256.

The light traps 1102 can be part of a changing pattern 322 of light projected onto an inner surface 242 of the flow region 240 of the microfluidic device 200 as discussed above with respect to FIGS. 3A and 3B. Once a selected biological micro-object 1002 is in a pen 256, the light trap 1102 corresponding to that biological micro-object 1002 can be turned off as illustrated in FIG. 14. The detector 224 can capture images of all or part of the flow region 240, including images of the selected and unselected biological micro-objects 1002, 1004, the channel 252, and the pens 256, and those images can facilitate identifying, trapping, and moving individual selected biological micro-objects 1002 into specific pens 256. The detector 224 and/or the selector 222 (e.g., configured as the DEP device of FIGS. 3A and 3B) can thus be one or more examples of a separating means for micro-objects that test positive for a first characteristic (e.g., selected biological micro-objects 1002) from micro-objects that test negative for the first characteristic (e.g., unselected biological micro-objects 1004).

As shown in FIG. 14, with the selected biological micro-objects 1002 in the pens 256, a flow 804 (e.g., a bulk flow) of the medium 244 can flush the unselected biological micro-objects 1004 out of the channel 252. As noted, after loading the biological micro-objects 904 into the channel 252 at step 102, the flow 804 of medium 252 can be stopped or slowed. As part of step 106, the flow 804 can be resumed or increased to flush the unselected biological micro-objects 1004 out of the channel 252 and, in some examples, out of the microfluidic device 200 (e.g., through the outlet 210).

The selected biological micro-objects 1202, 1204, 1206 can be moved into the isolation regions 444 of the sequestration pens 436, 438, 440 of the microfluidic device 400 in any of a number of possible ways. For example, as discussed above, the enclosure 402 of the microfluidic device can include DEP configurations, which can be utilized to capture and move particular ones of the biological micro-objects 904 in the sample material 902.

For example, as illustrated in FIG. 15, the control module 472 can map a path 1512, 1514, 1516 from the channel 434 to the isolation region 444 of one of the sequestration pens 436, 438, 440 for each of the selected biological micro-objects 1202, 1204, 1206. The control module 472 can then cause an DEP module (not shown) of the control/monitoring equipment 480 to generate and direct changing patterns of light into the microfluidic circuit 432 to capture and move the selected 1202, 1204, 1206 biological micro-objects along the paths 1512, 1514, 1516 into the isolation regions 444 of the sequestration pens 436, 438, 440. The control module 472 can also store in the memory 476 data identifying each of the selected biological micro-objects and the particular sequestration pens 436, 438, 440 into which each selected biological micro-object is moved.

Although one selected biological micro-object 1202, 1204, 1206 per pen 436, 438, 444 is shown in the example in of FIG. 15, more than one biological micro-object 1202, 1204, 1206 be moved into a single pen. Examples of numbers of biological micro-objects that can be moved from the sample material 902 into a single pen 136, 138, 140 include the following: 1, 2, 3, 4, 5, 1-50, 1-40, 1-30, 1-20, 1-10, 2-50, 2-40, 2-30, 2-20, 2-10, 3-50, 3-40, 3-30, 3-20, 3-10, 4-50, 4-40, 4-30, 4-20, 4-10, 5-50, 5-40, 5-30, 5-20, and 5-10. The foregoing are examples only, and other numbers of biological micro-objects 904 can be moved from the sample material 902 into a single pen 436, 438, 440.

In some embodiments, at least part of the sample material 902 can be loaded at step 104 into the isolation regions 444 of the pens 436, 438, 440. Also as part of step 104, the micro-objects 1202, 1204, 1206 can be selected in the isolation regions 144. In such embodiments, the sample material 902 including the unselected micro-objects 904 can be removed from the isolation regions 444 at step 106, leaving only the selected micro-objects 1202, 1204, 1206 in the isolation regions 444.

As illustrated in FIG. 16, the channel 434 can be cleared of the sample material 902 including unselected micro-objects 904 as part of step 106 by flushing the channel 434 with a flushing medium (not shown). In FIG. 16, the flow of a flushing medium through the channel 134 is labeled 1602. The flow 1602 of the flushing medium can be controlled so that the velocity of the flow 1602 is maintained below the maximum flow velocity $V_{max}$ corresponding to the maximum penetration depth $D_p$ as discussed above. As also discussed above, this will keep the selected biological micro-objects 1202, 1204, 1206 in the isolation regions 444 of their respective pens 436, 438, 440 and prevent material from the channel 434 or one of the pens 436, 438, 440 from contaminating another of the pens. In some embodiments, the flushing medium is flowed into a channel 434 having a cross-sectional area disclosed herein, e.g., about 3,000 to 6,000 square microns or about 2,500 to 4,000 square microns. The flushing medium can be flowed into the channel at a rate disclosed herein, e.g., about 0.05 to 5.0 µL/sec (e.g., about 0.1 to 2.0, 0.2 to 1.5, 0.5 to 1.0 µL/sec, or about 1.0 to 2.0 µL/sec). Clearing the channel 434 as part of step 106 can comprise flushing the channel 434 multiple times.

In some embodiments, the control module 472 can cause the control/monitoring equipment 480 to clear the channel 434. For example, the control module 472 can cause the control/monitoring equipment 480 to flow a flushing medium through a port 424 into the channel 434 and out of another port 424. The control module 472 can keep the velocity of the flow 1602 below the maximum flow velocity $V_{max}$. For example, for a channel 434 having a cross-sectional area of about 3,000 to 6,000 square microns (or about 2,500 to 4,000 square microns), the control module 472 can keep the velocity of the flow 1602 below a $V_{max}$ of 5.0 µL/sec (e.g., 4.0, 3.0, or 2.0 µL/sec).

After steps 102-106, the process 100 has sorted a mixture of biological micro-objects (e.g., 802, 904) in a microfluidic device (e.g., 200, 400) into selected biological micro-objects (e.g., 1004, 1202, 1204, 1206) and unselected biological micro-objects (e.g., 1004, 904). The process 100 has also placed the selected biological micro-objects in holding pens (e.g., 256, 436, 438, 440) in the microfluidic device and flushed the unselected biological micro-objects away. As discussed above, steps 102-106 can be repeated and thus performed k times, where k is one (in which case steps 102-106 are performed once but not repeated) or greater. The result can be numerous selected biological micro-objects in holding pens in the microfluidic device.

It is also noted that step 104 can be performed l times testing for up to l different characteristics before performing step 106, where l is a positive integer one or greater. For example, step 104 can test for a first characteristic of the biological micro-objects, such as size, shape, morphology, texture, visible markers, or the like, after which step 104 can be repeated to test for a subsequent characteristic, such as an assayable characteristic. Thus, the selected biological micro-objects can comprise biological micro-objects from the group(s) of biological micro-objects loaded at step 102 that test positive for as many as l different characteristics.

As noted, moving the selected biological micro-objects from the channel (e.g., 252, 434) into the pens and flushing the unselected biological micro-objects from the channel is but one example of how step 106 can be performed. Other examples include, moving the unselected biological micro-objects from the channel into the pens and flushing the selected biological micro-objects from the channel. For example, the selected biological micro-objects can be flushed from the channel and collected elsewhere in the microfluidic device or delivered to another device (not shown), where the selected biological micro-objects can be further processed. The unselected biological micro-objects can later be removed from the holding pens and discarded.

At step 108, the process 100 can perform a test on the selected biological micro-objects or biological micro-objects. This test can be a subsequent test (e.g., a second test) if a first test was performed as part of step 104. (Hereinafter, the test performed at step 108 is referred to as a "subsequent test" to distinguish from the "first test" referred to above in discussing step 104.) As noted above, the subsequent test performed at step 108 can test for the same characteristic (i.e., the first characteristic) as the first test of step 104 or a different characteristic. As also noted above, if the subsequent test performed at step 108 is for the first characteristic (and thus the same characteristic tested at step 104), the subsequent test can nevertheless be different than the first test. For example, the subsequent test can be more sensitive than the first test to detection of the first characteristic.

Figure 17:
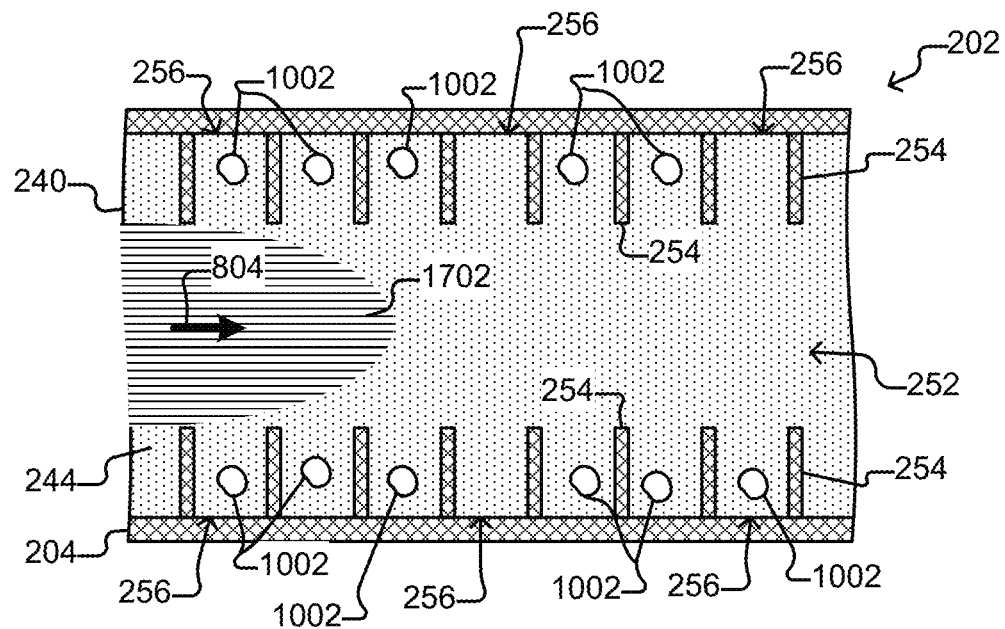
FIG. 17 is an example of providing an assay material to the biological micro-objects in the holding pens of the microfluidic device of FIGS. 2A-2C according to some embodiments of the invention.
Figure 18:
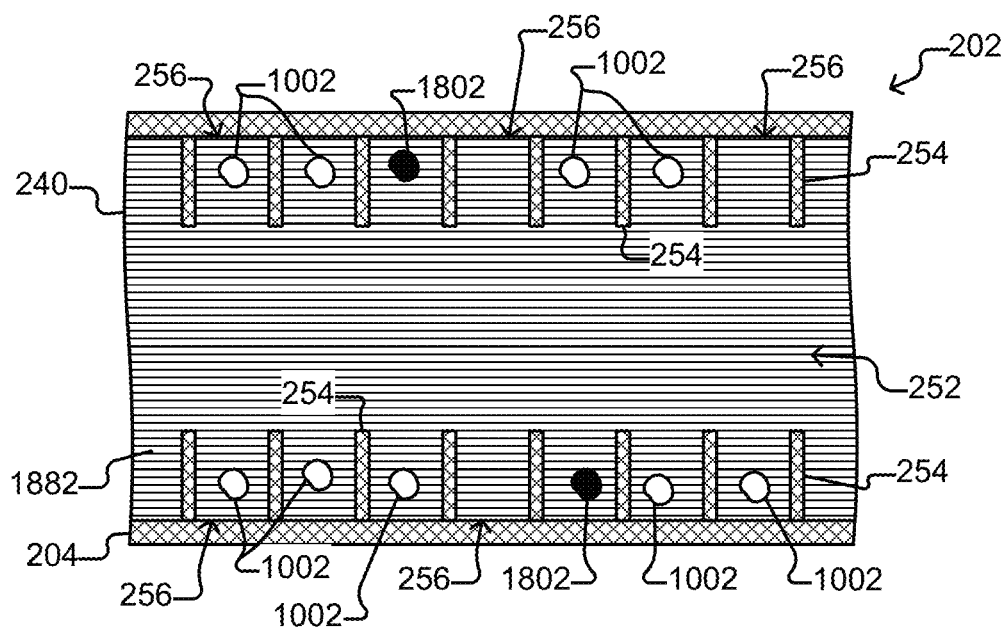
FIG. 18 illustrates the assay material diffused into the holding pens of the microfluidic device of FIGS. 2A-2C according to some embodiments of the invention.

FIGS. 17 and 18 illustrate an example in which the subsequent test performed at step 108 is performed in the microfluidic device 200 for an assayable characteristic that is different than the first characteristic tested at step 104. FIGS. 19-25 illustrate an example in which the test of step 108 is performed in the microfluidic device 400.

As illustrated in FIG. 17, an assay material 1702 can be flowed 804 into the channel 252 in sufficient quantity to expose the selected biological micro-objects 1002 in the pens 256 to the assay material 1702. For example, although the barriers 254 can impede the assay material 1702 from flowing directly from the channel 252 into the interior spaces of the pens 256, the assay material 1702 can enter the interior portions of the pens 256 and thus reach the selected biological micro-objects 1002 in the pens by diffusion. The assay material 1702 can comprise a material that reacts with the selected biological micro-objects 1002 that have the subsequent characteristic to produce a distinct, detectable condition. The assay material 1702 and the resulting distinct, detectable condition can be different than any assay material and condition discussed above with respect to the first testing at step 104. A washing buffer (not shown) can also be flowed into the channel 252 and allowed to diffuse into the pens 256 to wash the selected biological micro-objects 1002.

The detectable condition can be radiation of energy having one or more criteria such as threshold intensity, frequency in a particular frequency band, or the like. A color of the biological micro-objects 1002 is an example of radiating electromagnetic radiation in a particular frequency band. In the example shown in FIG. 18, selected biological micro-objects 1002 that test positive for the subsequent characteristic at step 108 continue to be labeled 1002, but the biological micro-objects that test negative (e.g., do not test positive) for the subsequent characteristic at step 108 are labeled 1802.

An example of the subsequent characteristic tested at step 410 can be viability of the biological micro-objects 1002. For example, the subsequent characteristic can be whether the biological micro-objects 1002 are alive or dead, and the assay material can be a viability dye such as 7-aminoactinomycin D. Such a dye can cause biological micro-objects 1002 that are alive to turn a particular color and/or dead biological micro-objects to turn a different color. The detector 224 (see FIGS. 2A-2C) can capture images of the biological micro-objects 1002 in the holding pens 256, and the control module 230 can be configured to analyze the images to determine which biological micro-objects exhibit the color corresponding to live biological micro-objects 1002 and/or which exhibit the color corresponding to dead biological micro-objects 1002. Alternatively, a human operator can analyze the images from the detector 224. The detector 224 and/or the control module 230 so configured can thus be one or more examples of a testing means for testing micro-objects in a liquid medium in a flow path in a microfluidic device for a particular characteristic (e.g., the first characteristic or a subsequent characteristic).

Figure 19:
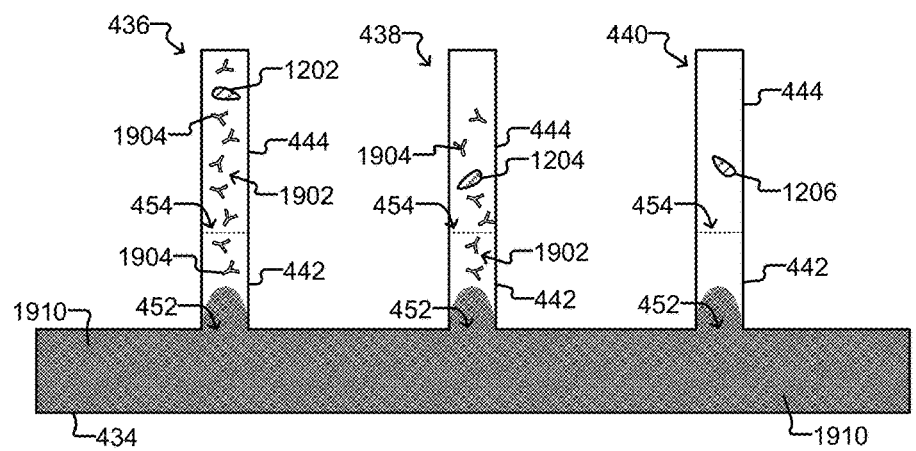
FIG. 19 shows an example of assay material in the channel of the microfluidic device of FIGS. 4A-4C and biological micro-objects in sequestration pens producing an analyte of interest according to some embodiments of the invention.

FIG. 19 illustrates an example in which the test performed at step 108 is for an analyte of interest 1902 produced by the selected biological micro-objects 1202, 1204, 1206 in isolation pens 236, 238, 240 of the microfluidic device 400. Components of the analyte of interest 1902 are labeled 1904 in FIG. 19. The analyte of interest can be, for example, proteins, nucleic acids, carbohydrates, lipids, metabolites, or other molecules secreted or otherwise released by specific cell types (e.g., healthy cells, cancer cells, virus- or parasite-infected cells, cells exhibiting an inflammatory response, or the like). Particular analytes of interest can be, for example, growth factors, cytokines (e.g., inflammatory or otherwise), viral antigens, parasite antigens, cancer cell-specific antigens, or therapeutic agents (e.g., therapeutic agents, such as hormones or therapeutic antibodies).

In the example illustrated in FIG. 19, step 108 can include loading an assay material 1910 into the microfluidic device 400 and detecting localized reactions, if any, of analyte components 1904. Step 108 can also include providing an incubating period after loading the assay material 1910 into the channel 434.

As shown in FIG. 19, the assay material 1910 can substantially fill the channel 434 or at least areas immediately adjacent to the proximal openings 442 of the pens 436, 438, 440. Also, the assay material 110 can extend into the connection regions 442 of at least some of the sequestration pens 436, 438, 440. In some embodiments, the assay material is flowed into a channel 434 having a cross-sectional area disclosed herein, e.g., about 3,000 to 6,000 square microns or about 2,500 to 4,000 square microns. The assay material can be flowed into the channel at a rate disclosed herein, e.g., about 0.02 to 0.25 µL/sec (e.g., about 0.03 to 0.2 µL/sec, or about 0.05 to 0.15 µL/sec, with slower speeds used for biological cellular assay materials and higher speeds used for non-cellular assay materials). Once the assay material 1910 is loaded into place in the channel 434, flow in the channel 434 can be slowed or substantially stopped.

The assay material 1910 can be flowed into the channel 434 sufficiently fast so that the assay material 1910 is in place adjacent to the proximal openings 452 of the pens 436, 438, 440 before analyte components 1904 produced in any of the pens 436, 438, 440 can diffuse into the channel 434. This can avoid a problem of analyte components 1904 from one pen 436, 438, 440 contaminating the channel 434 and/or other pens between the time when selected biological micro-objects 1202, 1204, 1206 are disposed into the pens 436, 438, 440 and completion of the loading of the assay material 1910 into the channel 434.

The velocity at which the assay material 1910 is loaded into the channel 434 can thus be at least a minimum flow velocity $V_{min}$ that fully loads the assay material 1910 into place adjacent to the proximal openings 452 over a time period $T_{load}$ that is less than a minimum time period $T_{diff}$ for a substantial amount of analyte components 1904 to diffuse from an isolation region 444 of a pen 436, 438, 440 into the channel 434. A "substantial amount" as used in this context means a detectable amount of analyte components that is sufficient to interfere with accurate detection of which sequestration pen the analyte components came from). The minimum flow velocity $V_{min}$ can be a function of a variety of different parameters. Examples of such parameters include the length of the channel 434, the length $L_{con}$ of a connection region 442 of a pen 436, 438, 440, a diffusion rate of analyte components 1904, medium viscosity, ambient temperature, or the like. Examples of the minimum flow velocity $V_{min}$ include at least about 0.04 µL/sec (e.g., at least about 0.10, 0.11, 0.12, 0.13, 0.14 µL/sec, or higher).

The minimum flow velocity $V_{min}$ for loading assay material 1910 into the channel 434 can be less than the maximum flow velocity $V_{max}$ corresponding to a penetration depth $D_p$ that is less than the length $L_{con}$ of a connection region 442 of a pen 436, 438, 440 as discussed above. For example, a ratio of $V_{max}/V_{min}$ can be in any of the following ranges: about 1, 2, 3, 4, 5, 6, 7, 8, 9, 10, 15, 20, 25, 30, 40, 50, 100, or more.

The incubation period provided after loading the assay material 1910 can be sufficient for the biological micro-objects 1202, 1204, 1206 to produce the analyte of interest 1902 and for analyte components 1904 to diffuse from the isolation regions 444 of the pens 436, 438, 440 to corresponding connection regions 442 or proximal openings 452. For example, the incubation period can provide analyte components 1904 sufficient time to diffuse into the channel 434.

The incubation period can comprise merely passively allowing the biological micro-objects 1202, 1204, 1206 to naturally produce the analyte of interest 1902 in the sequestration pens 436, 438, 440. Alternatively, the incubation period can comprise actively stimulating the biological micro-objects 1202, 1204, 1206 to produce the analyte of interest 1902 by, for example, providing nutrients, growth factors, and/or inductive factors to the biological micro-objects 1202, 1204, 1206; controlling the temperature, chemical composition, pH, or the like of the medium in the isolation regions 444 of the sequestration pens 436, 438, 440; directing stimulating energy such as light into the isolation regions 444; or the like.

The term "incubation" and "incubate," as used herein, cover the foregoing range from merely passively allowing the biological micro-objects 1202, 1204, 1206 to naturally produce analyte 1902 in the sequestration pens 436, 438, 440 to actively stimulating production of the analyte. Stimulating the production of analyte 1902 can also include stimulating the growth of a biological micro-object 1202, 1204, 1206. Thus, for example, biological micro-objects 1202, 1204, 1206 can be stimulated to grow prior to and/or while they are being stimulated to produce an analyte of interest 1902. If the biological micro-objects 1202, 1204, 1206 have been loaded into sequestration pens 436, 438, 440 as single biological micro-objects, growth stimulation can result in the production of clonal biological micro-object populations which express and/or secrete (or can be stimulated to express and/or secrete) an analyte of interest.

In some embodiments, the control module 472 can cause the control/monitoring equipment 480 to perform one or more actions during the incubation period 150. For example, the control module 472 can cause the control/monitoring equipment 480 to provide growth medium and/or inductive medium either periodically or as a continuous flow. Alternatively, control module 472 can cause the control/monitoring equipment 480 to incubate the biological micro-objects for a period of time sufficient for the analyte of interest to diffuse into the channel 434. For example, in the case of a protein analyte such as an antibody, the control module 472 can provide time for diffusion equal to around 2 seconds for every 1 micron that the biological micro-object is separated from the channel 434. For proteins and other analytes significantly smaller than an antibody, the time needed for diffusion may be smaller, such as 1.5 seconds for every 1 micron, or less (e.g., 1.25 s/µm, 1.0 s/µm, 0.75 s/µm, 0.5 s/µm, or less). Conversely, for proteins or other analytes significantly larger than an antibody, the time allotted for diffusion may be larger, such as 2.0 seconds for every micron, or more (e.g., 2.25 s/µm, 2.5 s/µm, 2.75 s/µm, 3.0 s/µm, or more).

It is noted that the incubation period can continue during performance of subsequent steps of the process 100. Also, the incubation period can begin prior to completion of step 106 (e.g., during any of steps 102-106).

Figure 20:
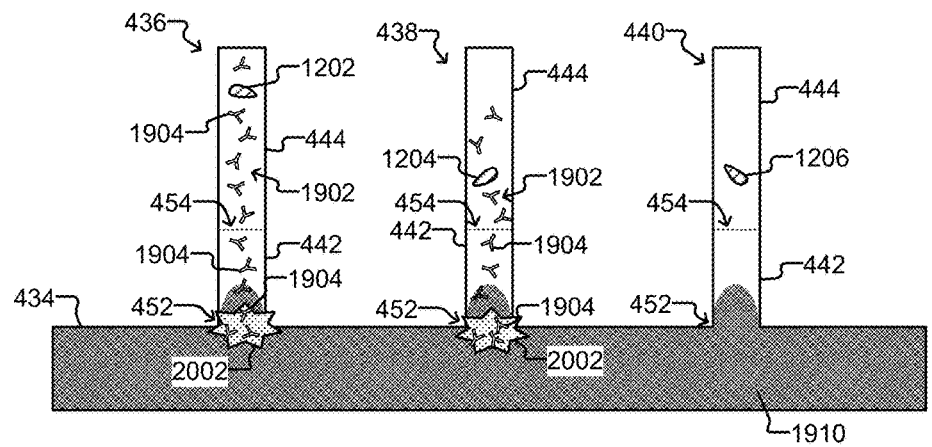
FIG. 20 illustrates an example of components of the analyte of interest diffusing out of isolation regions of sequestration pens and reacting with assay material adjacent to the proximal openings to a channel in the microfluidic device of FIGS. 4A-4C according to some embodiments of the invention.

The assay material 1910 can be configured both to interact with analyte components 1904 of an analyte of interest 902 and to produce a detectable reaction from the interaction. As illustrated in FIG. 20, analyte components 1904 from biological micro-objects 1202, 1204 in sequestration pens 436, 438 interact with the assay material 1910 adjacent to the proximal openings 452 of the sequestration pens 436, 438 to produce localized, detectable reactions. The biological micro-object 1206 in sequestration pen 440 does not, however, produce the analyte of interest 1902. Consequently, no such localized reaction (e.g., like 2002) occurs adjacent to the distal opening 452 of sequestration pen 440.

The localized reactions 2002 can be detectable reactions. For example, the reactions 2002 can be localized luminescence (e.g., fluorescence). Moreover, the localized reactions 2002 can be sufficiently localized and separated to be separately detectable by a human observer, a camera (not shown) in the control/monitoring equipment 480 of FIG. 4A, or the like. For example, the channel 434 can be sufficiently filled with the assay material 1910 that reactions (e.g., like 2002) are localized, that is, limited to space immediately adjacent to the proximal opening 452 of a corresponding sequestration pen 436, 438. As will be seen, the reactions 2002 can be from an aggregation of multiple components of the assay material 1910 immediately adjacent one or more of the proximal openings 452 of the sequestration pens 436, 438, 440.

Proximal openings 452 of contiguous sequestration pens 436, 438, 440 can be spaced apart by at least a distance $D_s$ (see FIG. 4C) that is sufficient to render localized reactions (e.g., like 2002) at adjacent distal openings 452 distinguishable one from another, for example, by a human observer, in images captured by a camera, or the like. Examples of suitable distances $D_s$ between proximal openings 452 of contiguous sequestration pens 436, 438, 440 include at least 20, 25, 30, 35, 40, 45, 50, 55, 60 microns, or more. Alternatively, or in addition, components of the assay material 910 (e.g., capture micro-objects, such as biological micro-objects, beads, and the like) can be organized in front of sequestration pens. For example, using DEP forces or the like, capture micro-objects can be grouped together and concentrated in regions of the channel 434 located adjacent to the proximal openings 452 of sequestration pens 436, 438, 440.

As noted, the assay material 1910, including components such as capture micro-objects (e.g., biological micro-objects, beads, or the like), can enter and thus be disposed at least in part in the connection regions 442 of the sequestration pens 436, 438, 440. In such a case, the reactions 2002, 2004 can occur entirely, substantially entirely, or partially in the connection regions 442 as opposed to substantially entirely in the channel 434. Moreover, capture micro-objects (e.g., biological micro-objects, beads, or the like) in the assay material 1910 can be disposed into isolation regions 444. For example, DEP forces or the like can be used to select and move capture micro-objects into isolation regions 444. For capture micro-objects that are disposed in the isolation region of a sequestration pen, the capture micro-objects can be disposed proximal to the biological micro-object(s) and/or in a portion (e.g., a sub-compartment) of the isolation region that is distinct from the portion occupied by the biological micro-object(s).

The assay material 1910 can be any material that specifically interacts, either directly or indirectly, with the analyte of interest 1902 to produce a detectable reaction (e.g., 2002). FIGS. 19-23 illustrate examples in which the analyte comprises an antibody with two antigen-binding sites. As persons skilled in the art will understand, the same examples could be readily adapted for situations in which the analyte of interest is something other than an antibody with two-antigen-binding sites.

Figure 21:
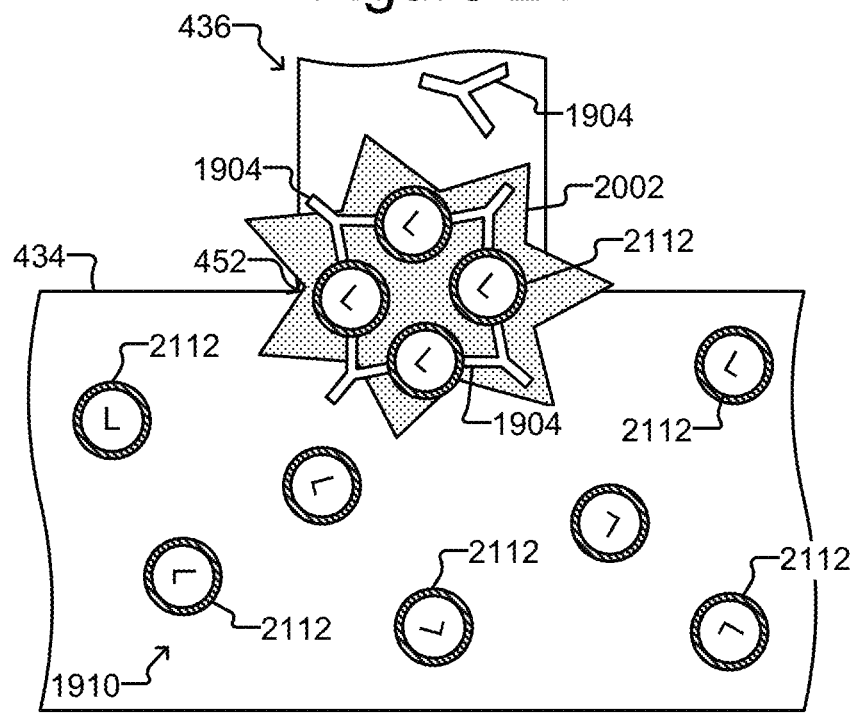
FIG. 21 is an example of an assay material comprising labeled capture micro-objects in the microfluidic device of FIGS. 4A-4C according to some embodiments of the invention.

FIG. 21, which shows part of the channel 434 and the proximal opening 452 of the sequestration pen 436, illustrates an example of the assay material 1910 comprising labeled capture micro-objects 2112. Each labeled capture micro-object 2112 can comprise both a binding substance capable of specifically binding analyte components 1904 and a labeling substance. As analyte components 1904 diffuse towards the proximal opening 452 of the sequestration pen 436, labeled capture micro-objects 2112 immediately adjacent to the opening 452 (or within the sequestration pen) can bind the analyte components 1904, which can result in a localized reaction 2002 (e.g., aggregation of the labeled capture micro-objects 2112) immediately adjacent (or internal to) the proximal opening 452.

Binding of analyte components 1904 to labeled capture micro-objects 2112 is greatest when the labeled capture micro-objects 2112 are immediately adjacent or internal to a proximal opening 452. This is because the concentration of analyte components 1904 is highest in isolation region 444 and connection region 442, thereby favoring binding of the analyte components 1904 to the labeled capture micro-objects 2112 and facilitating their aggregation in those regions. As analyte components 1904 diffuse out into the channel 234 and away from the proximal opening 252, their concentration goes down. As a result, fewer analyte components 1904 bind to labeled capture micro-objects 2112 that are located away from the proximal opening 252. The reduction in binding of analyte components 1904 to labeled capture micro-objects 2112 results, in turn, in reduced aggregation of the labeled capture micro-objects 2112 located away from the proximal opening 452. Labeled capture micro-objects 2112 that are not immediately adjacent (or internal) to a proximal opening 452 of a pen 436, 438, 440 thus do not produce a detectable localized reaction 2002 (or produce a localized reaction 2002 that is detectably lower in magnitude than the localized reaction 2002 that takes place immediately adjacent or internal to the proximal opening 452).

For analyte components that do not have two binding sites for a binding substance on the labeled capture micro-objects 2112, the labeled capture micro-objects could include two different binding substances (as discussed below and shown in FIG. 23), each of which is capable of being specifically bound by the analyte components. Alternatively, the assay could work if the analyte components multimerize (e.g., form homodimers, homotrimers, etc.).

Examples of labeled capture micro-objects 2112 include both inanimate and biological micro-objects. Examples of inanimate micro-objects include micro-structures such as microbeads (e.g., polystyrene microbeads), microrods, magnetic beads, quantum dots, and the like. The micro-structures can be large (e.g., 10-15 microns in diameter, or larger) or small (e.g., less than 10, 9, 8, 7, 6, 5, 4, 3, 2, or 1 microns in diameter, or smaller). Examples of biological micro-objects include biological micro-objects (e.g., reporter biological micro-objects), liposomes (e.g., synthetic or derived from membrane preparations), microbeads coated with liposomes, lipid nanorafts (see, e.g., Ritchie et al. (2009) "Reconstitution of Membrane Proteins in Phospholipid Bilayer Nanodiscs," Methods Enzymol., 464:211-231), and the like.

Figure 22:
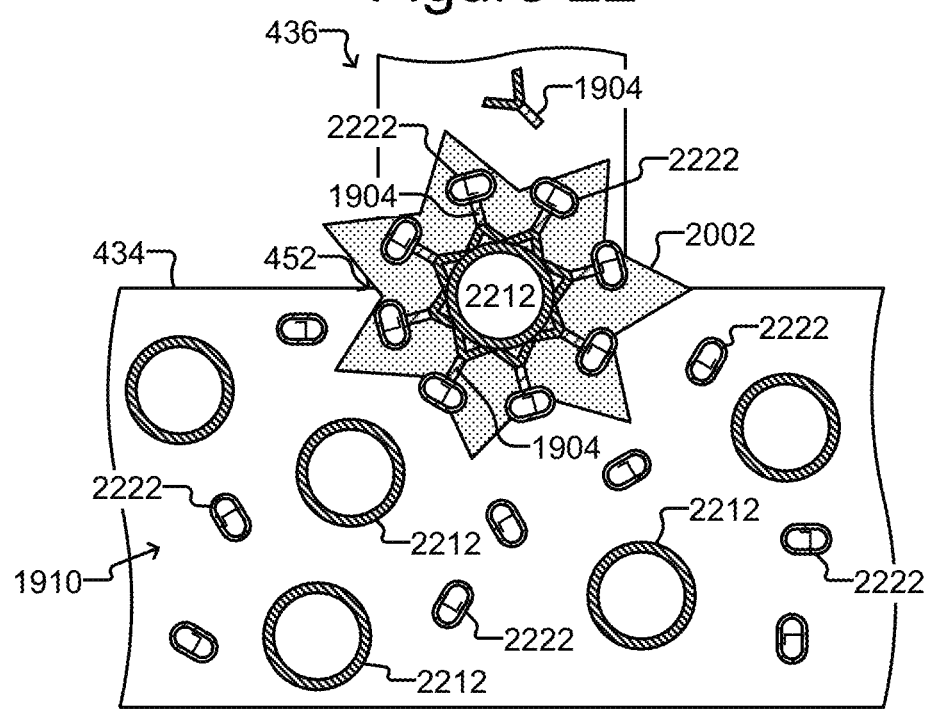
FIG. 22 is an example of an assay material comprising a mixture of capture micro-objects and a labeling agent in the microfluidic device of FIGS. 4A-4C according to some embodiments of the invention.
Figure 23:
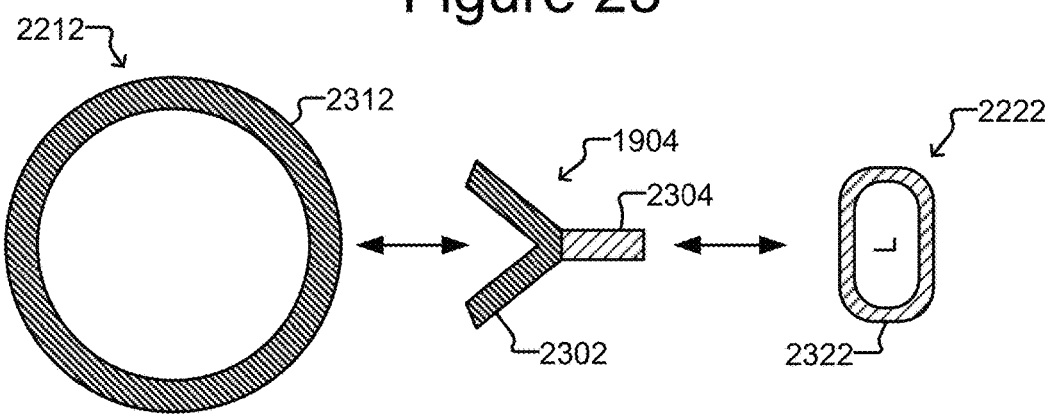
FIG. 23 illustrates examples of a capture micro-object, a component of the labeling agent, and the analyte of interest of FIG. 22 according to some embodiments of the invention.

FIG. 22 illustrates an example of the assay material 1910 comprising a mixture of capture micro-objects 2212 and labeling agent, components of which are identified as 2222 and referred to hereinafter as "labels 2222". FIG. 23 shows example configurations of a capture micro-object 2212, an analyte component 1904, and a label 2222. The capture micro-object 2212 can comprise a first affinity agent 2312 that specifically binds a first region 2302 of the analyte component 1904. The label 2222 can comprise a second affinity agent 2322 that specifically binds a second region 2304 of the analyte component 1904. As illustrated in FIG. 22, a reaction 2002 occurs when the first region 2302 of an analyte component 1904 binds to the first affinity agent 2312 of a capture micro-object 2212 and the second region 2304 of the analyte component 1904 binds to the second affinity agent 2322 of a label 2222.

As analyte components 1904 produced by the biological micro-object 1202 in the isolation region 444 of sequestration pen 436 diffuse towards the proximal opening 452, the analyte components 1904 can bind to a capture micro-object 2212 and a label 2222 immediately adjacent (or internal) to opening 452, thereby resulting in accumulation of label 2112 on the surface of the capture micro-object 2212. Binding of analyte components 1904 to labeled capture micro-objects 2212 is greatest when the capture micro-objects 2212 are immediately adjacent (or internal) to a proximal opening 452. Similar to the discussion above, this is because the relatively high concentration of analyte components 1904 in isolation region 444 and connection region 442 facilitate the binding of analyte components 1904 to the capture micro-objects 2212 and concomitant association of label 2222 at the surface of the capture micro-objects 2212. As analyte components 1904 diffuse out into the channel 434 and away from the proximal opening 452, the concentration goes down and fewer analyte components 1904 bind to capture micro-objects 2212 that are located away from the proximal opening 452. The reduction in binding of analyte components 1904 to capture micro-objects 2212 results in reduced accumulation of label 2222 at the surface of the capture micro-objects 2112 located away from the proximal opening 452. Accordingly, capture micro-objects 2212 that are not immediately adjacent (or internal) to a proximal opening 452 of a pen 436, 438, 440 do not become detectably labeled or, to the extent that they do become labeled, the labeling is detectably lower in magnitude than the labeling that takes place immediately adjacent or internal to the proximal opening 452.

Examples of capture micro-objects 2212 include all of the examples identified above for labeled capture micro-object 2112. Examples of the first affinity agent 2312 include a receptor that specifically recognizes the analyte components 1904 or a ligand that is specifically recognized by the analyte components 1904. For example, in the case of an antibody analyte, the first affinity agent 2312 can be an antigen of interest.

Examples of labels 2222 include labeling agents comprising luminescent labels (e.g., fluorescent labels) and labeling agents comprising enzymes capable of cleaving a signal molecule that fluoresces upon cleavage.

Figure 24:
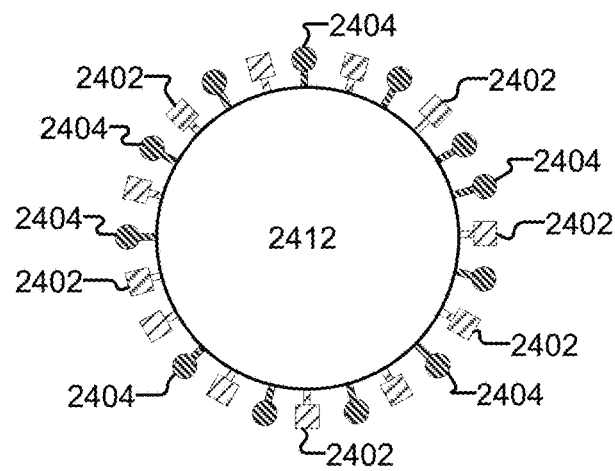
FIG. 24 shows an example of a composite capture micro-object comprising multiple affinity agents according to some embodiments of the invention.

Examples of the assay material 1910 include assay materials comprising composite capture micro-objects that include multiple affinity agents. FIG. 24 illustrates an example of a composite capture micro-object 2412 that comprises a first affinity agent 2402 and a second affinity agent 2404. The first affinity agent 2402 can be capable of specifically binding the first region 2302 of an analyte component 1904 (see FIG. 23), and the second affinity agent 2404 can be capable of specifically binding the second region 2304 of the same analyte component 1904 or a different analyte component. Moreover, the first affinity agent 2402 and the second affinity agent 2404 can optionally bind the first region 2302 and second region 2304 of an analyte component 1904 at the same time.

Examples of the first affinity agent 2402 include those discussed above. Examples of the second affinity agent 2404 include a receptor that specifically recognizes the second region 2304 of the analyte components 1904 or a ligand that is specifically recognized by the second region 2304 of the analyte components 1904. For example, in the case of an antibody analyte, the second affinity agent 2404 can bind to the constant region of an antibody. Examples of the foregoing include an Fc molecule, an antibody (e.g., an anti-IgG antibody), Protein A, Protein G, and the like.

Another example of the assay material 1910 is one that comprises multiple capture micro-objects. For example, the assay material 1910 can comprise first capture micro-objects (not shown) comprising the first affinity agent 2402 and second capture micro-objects (not shown) comprising the second affinity agent 2404. The first capture micro-objects can be different than the second capture micro-objects. For example, the first capture micro-objects can have a size, color, shape, or other characteristic that distinguishes the first capture micro-objects from the second capture micro-objects. Alternatively, the first capture micro-objects and the second capture micro-objects can be substantially the same type of capture micro-objects, with the exception of the type of affinity agent each comprises.

Another example of the assay material 1910 is one that comprises multiple types of capture micro-objects, each of which is designed to bind to a different analyte of interest. For example, the assay material 1910 can comprise first capture micro-objects (not shown) comprising a first affinity agent and second capture micro-objects (not shown) comprising a second affinity agent, wherein the first and second affinity agents do not bind to the same analyte of interest. The first capture micro-objects can have a size, color, shape, label, or other characteristic that distinguishes the first capture micro-objects from the second capture micro-objects. In this manner, multiple analytes of interest can be screened for at the same time.

Regardless of the specific content of the assay material 1910, in some embodiments, the control module 472 can cause the control/monitoring equipment 480 to load the assay material 1910 into the channel 434. The control module 472 can keep the flow of the assay material 1910 in the channel 434 between the minimum flow velocity $V_{min}$ and the maximum flow velocity $V_{max}$ discussed above. Once the assay material 1910 is in place adjacent to the proximal openings 452 of the pens 436, 438, 440, the control module 472 can substantially stop the flow of the assay material 1910 in the channel 434.

Performed in the microfluidic device 400, step 108 can include detecting localized reactions 2002 immediately adjacent to one or more of the proximal openings 452 of the sequestration pens 436, 438, 440 that indicate reaction of analyte components 1904 with the assay material 1910 loaded into the channel 434. If localized reactions 2002 are detected immediately adjacent to any of the proximal openings 452 of the sequestration pens 436, 438, 440, it can be determined whether any of those detected localized reactions 2002 indicate positive performance of one or more of the biological micro-objects 1202, 1204, 1206 in the sequestration pens 436, 438, 440. In some embodiments, a human user can observe the channel 434 or connections regions 442 of the pens 436, 438, 440 to monitor for and determine whether localized reactions 2002 indicate positive performance of biological micro-object 1202, 1204, 1206. In other embodiments, the control module 472 can be configured to do so. The process 2500 of FIG. 25 is an example of operation of the control module 472 for performing to monitor for and determine whether localized reactions 2002 indicate positive performance of biological micro-object 1202, 1204, 1206.

At step 2502, the control module 472 performing the process 2500 can capture at least one image of the channel 434 or connection regions 442 of the sequestration pens 436, 438, 440 with a camera or other image capture device (not shown but can be an element of the control/monitoring equipment 480 of FIG. 4A). Examples of exposure times for capturing each image include 10 ms to 2 seconds, 10 ms to 1.5 seconds, 10 ms to 1 second, 50 to 500 ms, 50 to 400 ms, 50 to 300 ms, 100 to 500 ms, 100 to 400 ms, 100 to 300 ms, 150 to 500 ms, 150 to 400 ms, 150 to 300 ms, 200 to 500 ms, 200 to 400 ms, or 200 to 300 ms. The control module 472 can capture one such image or multiple images. If the control module 472 captures one image, that image can be the final image referred to below. If the control module 472 captures multiple images, the control module 472 can combine two or more of the captured images into a final image. For example, the control module 472 can average two or more of the captured images. In some embodiments, the control module 472 can capture and average at least 10, 20, 30, 40, 50, 60, 70, 80, 90, 100, 110, 120, 130, 140, 150, 160, 170, 180, 190, 200, or more of the captured images to produce the final image.

At step 2504, the control module 472 can identify in the final image any indications of localized reactions 2002. As discussed above, examples of the localized reactions 2002 include luminescence (e.g., fluorescence), and the control module 472 can thus analyze the final image for luminescence immediately adjacent to any of the proximal openings 452 of the sequestration pens 436, 438, 440. The control module 472 can be programmed to utilize any image processing technique to identify localized reactions 2002 in the final image. In the example, illustrated in FIG. 20, the control module 472 can detect the localized reactions 2002 immediately adjacent to the proximal openings 452 of sequestration pens 436, 438.

At step 2506, the control module 472 can correlate each localized reaction 2002 detected at step 2504 to a corresponding sequestration pen 436, 438, 440. For example, the control module 472 can do so by correlating each localized reaction 2002 detected at step 2504 to the sequestration pen 436, 438, 440 with the nearest proximal opening 452 to the reaction 1002. In the example of FIG. 20, the control module 472 can correlate the reactions 2002 to the sequestration pens 436, 438.

The control module 472 can perform steps 2508 and 2510 of FIG. 25 for each sequestration pen 436, 438, 440 to which a detected reaction was correlated at step 2506. With respect to the example of FIG. 20, the control module 472 can thus perform steps 2508 and 2510 for sequestration pen 436 and then repeat steps 2508 and 2510 for sequestration pen 438.

At step 2508, the control module 472 can determine whether the detected reaction 1002 correlated to the current sequestration pen 436 indicates a positive result for the biological micro-object(s) 1202 in the current pen 436. For example, the control module 472 can extract data regarding the detected reaction 1002 from the final image obtained at step 2502, and determine whether the extracted data indicates a positive result. Any number of different criteria can be used. For example, the detected reaction 2002 can be luminescence, and the criteria for determining a positive result can include intensity of the luminescence exceeding a threshold, brightness of the luminescence exceeding a threshold, color of the luminescence falling within a predetermined color range, or the like. If at step 2508, the control module 472 determines that the detected reaction is positive, the control module 472 can proceed to step 2510, where the control module 472 can identify the current sequestration pen 436 as containing a positive biological micro-object 1202. If the determination at step 2508 is negative, the control module 472 can repeat step 2508 for the next sequestration pen 438 for which a detected reaction was correlated at step 2506.

In the example illustrated in FIG. 20, it is assumed that the localized reaction 2002 correlated to sequestration pen 436 is determined at step 2508 to be positive, but the localized reaction 2002 correlated to sequestration pen 438 is negative (e.g., luminescence is detected, but it is below the threshold for determining that sequestration pen 438 is positive). As previously noted, no reaction was detected adjacent to the proximal opening 452 of sequestration pen 440. Consequently, the control module 472 identifies only sequestration pen 436 as having a positive biological micro-object. Although not shown in FIG. 25, the control module 472 can, as part of process 2500, identify sequestration pens 438, 440 as negative.

Figure 27:
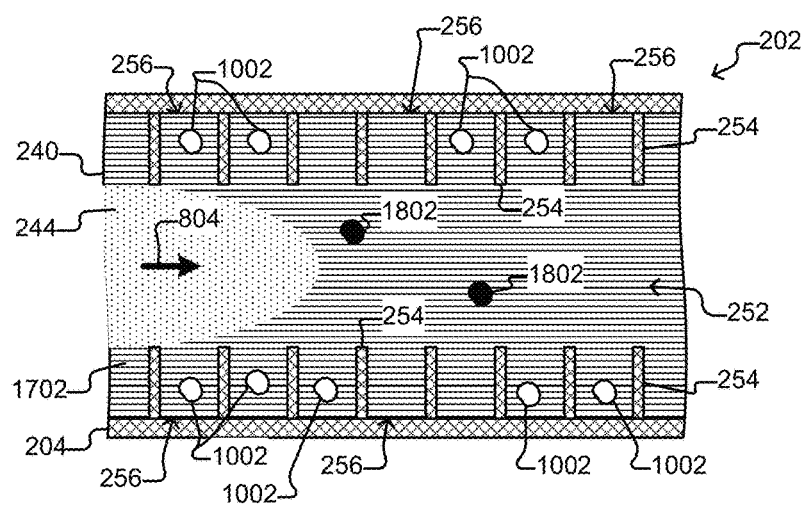
FIG. 27 shows flushing the negative biological micro-objects from the flow path in the microfluidic device of FIGS. 2A-2C according to some embodiments of the invention.
Figure 29:
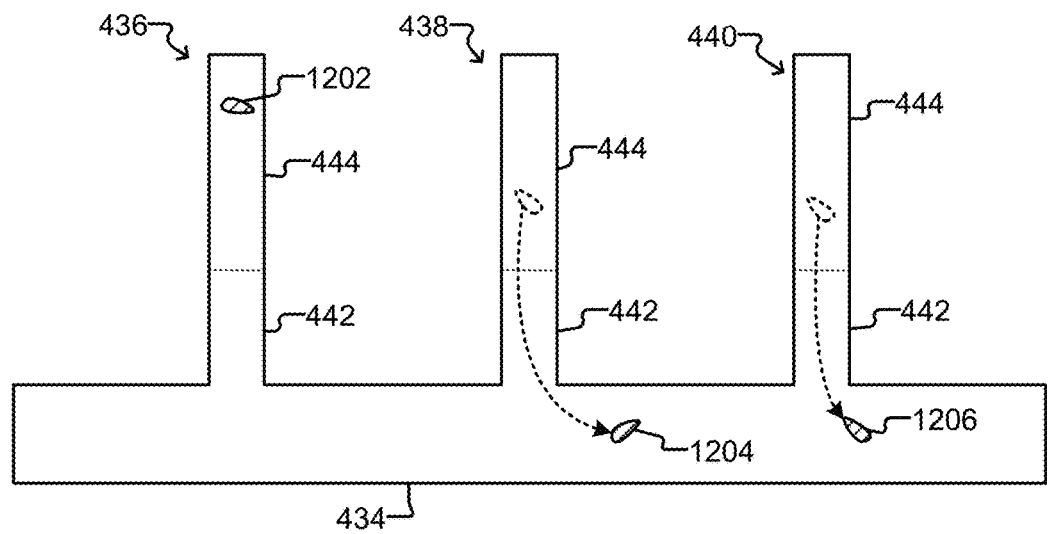
FIG. 29 is an example of separating negative biological micro-objects from positive biological micro-objects in the microfluidic device of FIGS. 4A-4C according to some embodiments of the invention.

Returning to FIG. 1, at step 110, the process 100 can separate the biological micro-objects that tested positive at step 108 from the biological micro-objects that tested negative. FIGS. 26 and 27 illustrate an example in which the biological micro-objects 1002 that tested negative for the subsequent characteristic at step 108 are moved into and then flushed out of the channel 252 of the microfluidic device 200. FIG. 29 shows an example in which negative biological micro-objects 1204, 1206 are separated from positive biological micro-object 1202 in the microfluidic device 400.

As shown in FIG. 26, each biological micro-object 1002 that tested negative at step 110 can be selected and trapped with a light trap 2602 in a holding pen 256. Negative micro-objects are labeled 1802 in FIG. 26. The light trap 2602 can then be moved from a holding pen 256 into the channel 252. As shown in FIG. 27, the traps 2602 can be turned off in the channel 252, and a flow 804 (e.g., a convection flow) of medium 244 can flush the negative biological micro-objects 1802 out of the channel 252 (and, optionally, out of the flow region 240). The assay material 1702 can diffuse out of the pens 256, and the flow 804 can also flush the assay material 1702 out of the channel 252.

The light traps 2602 can be generated and manipulated as discussed above. For example, as illustrated, each negative biological micro-object 2602 can be individually trapped and moved from a holding pen 256 into the channel 252. Alternatively, more than one negative biological micro-object 2602 can be trapped by a single trap 2602. For example, there can be more than one biological micro-object 2602 in a single pen 256. Regardless, two or more of the negative biological micro-objects 2602 can be selected in the pens 256 and moved in parallel into the channel 252.

The detector 224 can capture images of all or part of the flow region 240 including images of the biological micro-objects 1002 in the pens 256, and those images can facilitate identifying, trapping, and moving individual negative biological micro-objects 2602 out of specific pens 256 and into the channel 252. The detector 224 and/or the selector 222 (e.g., configured as the DEP device of FIGS. 3A and 3B) can thus be one or more examples of a separating means for micro-objects that test positive for a characteristic from micro-objects that test negative for the characteristic.

As shown in FIG. 27, with the negative biological micro-objects 1802 in the channel 252, a flow 804 of the medium 244 can flush the biological micro-objects 1802 out of the channel 252 and, in some examples, out of the microfluidic device 200 (e.g., through the outlet 210). For example, if the flow 804 was previously stopped or slowed, the flow 804 can be resumed or increased.

Alternatively, the biological micro-objects 1002 that tested positive at step 108 can be moved from the pens 256 into the channel 252 and flushed by the flow 804 from the channel 252 at step 110. In such an example, the biological micro-objects 1002 that tested positive at both steps 104 and 108 can be collected elsewhere in the microfluidic device 200 for storage, further processing, delivery to another device (not shown), or the like. The biological micro-objects 1802 that tested negative at step 108 can later be removed from the holding pens 256 and discarded.

Figure 28:
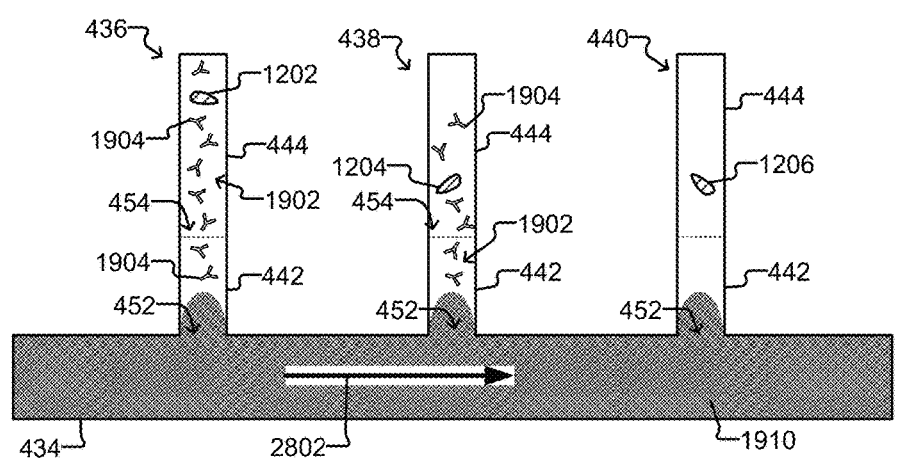
FIG. 28 illustrates an example of clearing the channel of assay material in the microfluidic device of FIGS. 4A-4C according to some embodiments of the invention.

As shown in FIGS. 28 and 29, the assay material 1910 can be flushed 2802 from the channel 434 (FIG. 28). Then, as shown in FIG. 29, the biological micro-objects 1204, 1206 in the microfluidic device 400 that tested negative at step 108 can be moved from sequestration pens 438, 440 into the channel 434 from where the negative biological micro-objects 1204, 1206 can be cleared from the channel 434 (e.g., by a flow of medium (not shown but can be like 2802 of FIG. 28) in the channel 434). The biological micro-objects 1204, 1206 can be moved from sequestration pens 438, 440 into the channel 434 in any manner discussed above (e.g., DEP, gravity, or the like) for moving biological micro-objects 1202, 1204, 1206 from the channel 434 into the sequestration pens 436, 438, 440.

After steps 108 and 110, the process 100 has further sorted the micro-objects (e.g., 1002, 1202, 1204, 1206) selected at step 104 in accordance with a test performed at step 108. Moreover, the micro-objects selected at step 104 that also tested positive to the subsequent test at step 108 can remain in the holding pens (e.g., 256, 436, 438, 440), while negative micro-objects can be removed.

As discussed above, steps 108 and 110 can be repeated and thus performed n times, where n is an integer one (in which case steps 108 and 110 are performed once but not repeated) or greater. The subsequent test performed at each repetition of step 108 can be a different test. Alternatively, the subsequent test performed at a repetition of step 108 can be the same test as was previously performed at step 104 or a prior performance of step 108. The biological micro-objects (e.g., biological micro-objects) loaded at step 102 can thus be subjected to a sequence of n+1 tests. In some embodiments, each of the n+1 tests can be a different test, and in some embodiments, each of the n+1 tests can test for a different characteristic. The process 100 can thus sort from initial mixtures of biological micro-objects a group that test positive to n+1 tests each of which can be different, and in some embodiments, the process 100 can sort from initial mixtures of biological micro-objects a group that test positive for n+1 different characteristics.

Alternatively, the process 100 can select biological micro-objects at step 104 and then rank the selected biological micro-objects according to the number of tests at step 108 (either performed simultaneously or by repeating step 108) in which the biological micro-objects test positive. Testing for multiple characteristics in this manner is desirable for numerous applications, including antibody characterization. For example, the multiple tests can help with any of the following: identifying conformation specific antibodies (e.g., the different tests can assess the ability of an antibody analyte to bind different conformation of a particular antigen); epitope mapping of an antibody analyte (e.g., using genetically or chemically altered antigen); assessing species cross-reactivity of an antibody analyte (e.g., different tests can assess the ability of antibody analyte to bind to homologous antigens originating from human, mouse, rat, and/or other animals (e.g., experimental animals); and IgG isotyping of an antibody analyte. The generation of chemically modified antigen for epitope mapping of antibodies has been described, for example, in Dhungana et al. (2009), Methods Mol. Biol. 524:119-34.

The entire process 100 can be repeated one or more times. Thus, after performing steps 108 and 110 n times, steps 102-106 can again be performed k times followed by n more performances of steps 108 and 110. The number k need not be the same number for each repetition of the process 100. Similarly, the number n need not be the same number for each repetition of the process 100. For example, the final repetition of steps 108 and 110 for a particular repetition of the process 100, the flow 804 shown in FIG. 27 can load a new mixture of biological micro-objects into the channel 252 of the microfluidic device 200 as illustrated in FIG. 8 and thus be part of step 102 for the next performance of the process 100 on the microfluidic device 200.

The process 100 can similarly be repeated multiple times on the microfluidic device 400. For example, the process 100 can be repeated to retest or reanalyze the positive biological micro-objects kept in their sequestration pens 436, 438, 440 at step 110; to retest or reanalyze positive biological micro-objects at reduced density (e.g., one biological micro-object per sequestration pen, assuming that the initial test was performed with multiple biological micro-objects per sequestration pen); to test or analyze new biological micro-objects loaded into the microfluidic device 400 at the next repetition of step 108; to test or analyze the positive biological micro-objects kept in their sequestration pens 436, 438, 440 at step 110 with respect to a different analyte material (e.g., by repeating step 108 with assay material 1910 designed to detect a second or additional analyte of interest); or the like.

Figure 30:
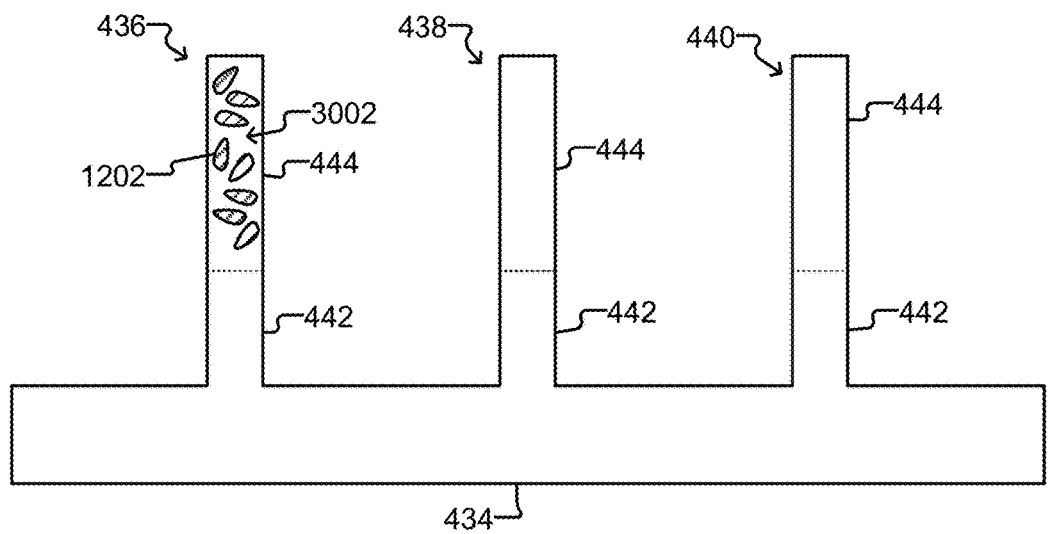
FIG. 30 shows an example of producing clonal biological micro-objects in a sequestration pen in the microfluidic device of FIGS. 4A-4C according to some embodiments of the invention.

FIG. 30 illustrates another example. As shown, after the step 110 has been performed, one or more of the biological micro-objects (e.g., 1202) kept in its sequestration pen (e.g., 436) can be allowed to produce a clonal colony 3002 of biological micro-objects in its sequestration pen (e.g., 436). All or part of the process 100 (e.g., steps 108 and 110) can then be used to test or analyze the colony 3002. Alternatively, the biological micro-objects can be separated and retested, as discussed above. In still other alternatives, the biological micro-objects can be allowed to grow into a colony before process 100 has been completed (e.g., after either of steps 106 or 108, but before step 110).

Although specific embodiments and applications of the invention have been described in this specification, these embodiments and applications are exemplary only, and many variations are possible. For example, the process 100 of FIG. 1 and the process 2500 of FIG. 25 are examples only, and variations are contemplated. Thus, for example, at least some of the steps of process 100 and/or process 2500 can be performed in a different order than shown, and some of the steps can be performed simultaneously or can otherwise overlap performance of others. As other examples, the processes 100, 2500 can include additional steps that are not shown or lack some of the steps that are shown.

EXAMPLES

Example 1

Screening Mouse Splenocytes for Secretion of IgG Antibodies Capable of Binding Human CD45

A screen was performed to identify mouse splenocytes that secrete IgG-type antibodies that bind to human CD45. The experimental design included the following steps:

1. Generation of CD45 antigen coated beads;
2. Harvest mouse splenocytes;
3. Load cells into a microfluidic device; and
4. Assay for antigen specificity.

Reagents used for the experiment included those shown in Table 1.

TABLE 1

Reagents

| | Name | Vendor | Catalog Number | Lot Number |
|---|---|---|---|---|
| 1 | Slide-A-Lyzer ™ MINI Dialysis Device, 7K MWCO, 0.1 mL | Thermo Pierce | 69560 | OJ189254 |
| 2 | CD45 Protein | R&D Systems | 1430-CD | 112722 |
| 3 | PBS pH 7.2 with Mg2+ and Ca2+ | Fisher Scientific | BP29404 | |
| 4 | SPHERO ™ Streptavidin Coated Beads (8 μm) | Spherotech | SVP-60-5 | AC01 |
| 5 | EZ-Link ™ NHS-PEG4-Biotin, No-Weigh ™ Format | Thermo Pierce | 21329 | |
| 6 | Hybridoma SFM Media | Life Technologies | 12045-076 | |
| 7 | Fetal Bovine Serum | Hyclone | #SH30084.03 | |
| 8 | Penicillin-Streptomycin (10,000 U/mL) | Life Technologies | 15140-122 | |
| 9 | Goat anti-mouse F(ab')2-Alexa Fluor ® 568 | Life Technologies | Cat# A11019 | Lot#1073003 |
| 10 | streptavidin-Alexa Fluor ® 488 | Life Technologies | Catalog #S32354 | Lot #1078760 |
| 11 | Mouse anti CD45 IgG$_1$ | R&D Systems | MAB1430 | ILP0612061 |
| 12 | BD Falcon ™ Cell Strainers, 40 μm, Blue | BD | 352340 | |

Generation of CD45 Antigen Coated Beads

CD45 antigen coated microbeads were generated in the following manner:

50 μg carrier free CD45 was resuspended in 500 μL PBS (pH 7.2).

A Slide-A-Lyzer™ mini cup was rinsed with 500 μL PBS, then added to a microfuge tube.

50 μL of the 0.1 μg/μL CD45 solution was added to the rinsed slide-a-lyzer mini cup.

170 μL PBS was added to 2 mg of NHS-PEG4-Biotin, after which 4.1 μL of NHS-PEG4-Biotin was added to the Slide-A-Lyzer™ mini cup containing the CD45 antigen.

The EZ-Link™ NHS-PEG4-Biotin was incubated with the CD45 antigen for 1 hour at room temperature.

Following the incubation, the Slide-A-Lyzer™ mini cup was removed from the microfuge tube, placed into 1.3 mls PBS (pH 7.2) in a second microfuge tube, and incubated at 4° C. with rocking, for a first 1 hour period. The Slide-A-Lyzer™ mini cup was subsequently transferred to a third microfuge tube containing 1.3 mls of fresh PBS (pH 7.2), and incubated at 4° C. with rocking, for a second 1 hour period. This last step was repeated three more times, for a total of five 1 hour incubations.

100 μL of biotinylated CD45 solution (~50 ng/μL) was pipetted into labeled tubes.

500 μL Spherotech SPHERO™ streptavidin coated beads were pipetted into a microfuge tube, washed 3 times (1000 μL/wash) in PBS (pH 7.4), then centrifuges for 5 min at 3000 RCF.

The beads were resuspended in 500 μl PBS (pH 7.4), resulting in a bead concentration of 5 mg/ml.

50 μL biotinylated protein was mixed with the resuspended Spherotech SPHERO™ streptavidin coated beads. The mixture was incubated at 4° C., with rocking, for 2 hours, then centrifuged 4° for 5 min at 3000 RCF. The supernatant was discarded and the CD45 coated beads were washed 3 times in 1 mL PBS (pH 7.4). The beads were then centrifuged at 4° C. for another 5 min at 3000 RCF. Finally, the CD45 beads were resuspended in 500 μL PBS pH 7.4 and stored at 4° C.

Mouse Splenocyte Harvest

The spleen from a mouse immunized with CD45 was harvested and placed into DMEM media+10% FBS. Scissors were used to mince the spleen.

Minced spleen was placed into a 40 μm cell strainer. Single cells were washed through the cell strainer with a 10 ml pipette. A glass rod was used to break up the spleen further and force single cells through the cell strainer, after which single cells were again washed through the cell strainer with a 10 ml pipette.

Red blood cells were lysed with a commercial kit.

Cells were spun down at 200×G and raw splenocytes were resuspended in DMEM media+10% FBS with 10 ml pipette at a concentration of 2e$^8$ cells/ml.

Loading Cells into Microfluidic Device

Splenocytes were imported into the microfluidic chip and loaded into pens containing 20-30 cells per pen. 100 μL of media was flowed through the device at 1 μL/s to remove unwanted cells. Temperature was set to 36° C., and culture media was perfused for 30 minutes at 0.1 μL/sec.

Antigen Specificity Assay

Cell media containing 1:2500 goat anti-mouse F(ab')2-Alexa Fluor® 568 was prepared.

100 μL of CD45 beads were resuspended in 22 μL of the cell media containing the 1:2500 dilution of goat anti-mouse F(ab')2-Alexa Fluor® 568.

The resuspended CD45 beads were next flowed into the main channel of the microfluidic chip at a rate of 1 μL/sec until they were located adjacent to, but just outside the pens containing splenocytes. Fluid flow was then stopped.

The microfluidic chip was then imaged in bright field to determine the location of the beads.

Next, a Texas Red Filter was used to capture images of the cells and beads. Images were taken every 5 minutes for 1 hr, with each exposure lasting 1000 ms and a gain of 5.

Results

Positive signal was observed developing on the beads, reflecting the diffusion of IgG-isotype antibodies diffusing out of certain pens and into the main channel, where they were able to bind the CD45-coated beads. Binding of anti-CD45 antibody to the beads allowed for the secondary goat anti-mouse IgG-568 to associate with the beads and produce a detectable signal. See FIGS. 31A-31C & white arrows.

Using the methods of the invention, each group of splenocytes associated with positive signal could be separated and moved into new pens as a single cell and reassayed. In this manner, single cells expressing anti-CD45 IgG antibodies could be detected.

In addition to any previously indicated modification, numerous other variations and alternative arrangements may be devised by those skilled in the art without departing from the spirit and scope of this description. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. As used herein, the examples and embodiments, in all respects, are meant to be illustrative only and should not be construed to be limiting in any manner. It should also be noted, that while the term step is used herein, that term may be used to simply draw attention to different portions of the described methods and is not meant to delineate a starting point or a stopping point for any portion of the methods, or to be limiting in any other way.

We claim:

1. A microfluidic device comprising an enclosure comprising:
   a base, a microfluidic circuit structure disposed on the base, and a cover which collectively define a microfluidic circuit, wherein said microfluidic circuit comprises:
      a flow region for containing a flow of a first fluidic medium;
      one or more inlets through which said first medium can be input into said flow region;
      one or more outlets through which said first medium can be removed from said flow region;
      a microfluidic channel comprising at least a portion of said flow region; and
      a microfluidic sequestration pen comprising:
         an isolation region for containing a second fluidic medium, the isolation region having a single opening; and
         a connection region fluidically connecting said isolation region to said flow region, wherein said connection region comprises a proximal opening into said microfluidic channel having a width $W_{con}$ ranging from about 20 microns to about 100 microns and a distal opening into said isolation region, and wherein a length $L_{con}$ of said connection region from said proximal opening to said distal opening is as least 1.0 times a width $W_{con}$ of said proximal opening of said connection region,
   wherein said isolation region of said microfluidic sequestration pen is an unswept region of said micro-fluidic device.

2. The device of claim 1, wherein a width of said microfluidic channel at said proximal opening of said connection region is between about 50 microns and about 500 microns.

3. The device of claim 1, wherein the length $L_{con}$ of said connection region from said proximal opening to said distal opening is at least 1.5 times the width $W_{con}$ of said proximal opening of said connection region.

4. The device of claim 1, wherein the length $L_{con}$ of said connection region from said proximal opening to said distal opening and the width $W_{con}$ of said proximal opening of said connection region are sized so that a penetration depth into said sequestration pen of said first medium flowing in said microfluidic channel at a flow rate no greater than 5.0 μL/sec is less than said length $L_{con}$.

5. The device of claim 1, wherein the length $L_{con}$ of said connection region from said proximal opening to said distal opening is between about 20 microns and about 500 microns.

6. The device of claim 1, wherein said proximal opening of said connection region is parallel to a direction of said flow of said first medium in said flow region.

7. The device of claim 1, wherein the length $L_{con}$ of said connection region from said proximal opening to said distal opening is at least 2.0 times the width $W_{con}$ of said proximal opening of said connection region.

8. The device of claim 1, wherein a height of said microfluidic channel at said proximal opening of said connection region is between 20 microns and 100 microns.

9. The device of claim 1, wherein said cover is an integral part of said microfluidic circuit structure.

10. The device of claim 1, wherein said cover and said base are part of a dielectrophoresis (DEP) mechanism for selectively inducing DEP forces on a micro-object.

11. The device of claim 1, wherein said microfluidic device further comprises a first electrode, an electrode activation substrate, and a second electrode, wherein said first electrode is part of a first wall of said enclosure and said electrode activation substrate and said second electrode is part of a second wall of said enclosure, wherein the electrode activation substrate comprises a photoconductive material, semiconductor integrated circuits, or phototransistors.

12. The device of claim 11, wherein said first wall of said microfluidic device is said cover, and wherein said second wall of said microfluidic device is said base.

13. The device of claim 11, wherein said electrode activation substrate comprises phototransistors.

14. The device of claim 1, wherein said cover and/or said base is transparent to light.

15. The device of claim 1, wherein barriers defining said microfluidic sequestration pen extend from a surface of said base of said microfluidic device to a surface of said cover of said microfluidic device.

16. The device of claim 1, wherein the volume of the isolation region ranges from about $1 \times 10^4$ to about $2 \times 10^6$ cubic microns.

* * * * *